(12) United States Patent
Bradley et al.

(10) Patent No.: US 6,979,728 B2
(45) Date of Patent: Dec. 27, 2005

(54) ARTICLES OF MANUFACTURE AND METHODS FOR ARRAY BASED ANALYSIS OF BIOLOGICAL MOLECULES

(75) Inventors: Allan Bradley, Cambridge (GB); Wei-Wen Cai, Pearland, TX (US); Upendra Marathi, Houston, TX (US)

(73) Assignees: Baylor College of Medicine, Houston, TX (US); Spectral Genomics, Inc., Houston, TX (US)

(*) Notice: Subject to any disclaimer, the term of this patent is extended or adjusted under 35 U.S.C. 154(b) by 216 days.

(21) Appl. No.: 09/853,343

(22) Filed: May 10, 2001

(65) Prior Publication Data

US 2002/0006623 A1 Jan. 17, 2002

Related U.S. Application Data

(63) Continuation-in-part of application No. 09/546,085, filed on Apr. 10, 2000, which is a continuation-in-part of application No. 09/071,876, filed on May 4, 1998, now Pat. No. 6,048,695.

(51) Int. Cl.$^7$ .......................... C07H 21/02; C07K 1/00; C01N 33/544
(52) U.S. Cl. ..................... 536/23.1; 530/402; 436/518
(58) Field of Search ............................ 536/23.1, 22.1; 530/402, 350; 436/518; 435/6

(56) References Cited

U.S. PATENT DOCUMENTS

| | | | |
|---|---|---|---|
| 4,231,910 A | * 11/1980 | Plueddemann | 260/29.4 |
| 4,713,116 A | * 12/1987 | Krinski et al. | 106/154.1 |
| 5,401,415 A | * 3/1995 | Rauh et al. | 210/660 |
| 5,472,842 A | 12/1995 | Stokke et al. | 435/6 |
| 5,665,549 A | 9/1997 | Pinkel et al. | 435/6 |
| 5,688,642 A | 11/1997 | Chrisey et al. | 435/6 |
| 5,807,756 A | 9/1998 | Bauman et al. | 435/6 |
| 5,830,645 A | * 11/1998 | Pinkel et al. | 435/6 |
| 5,851,769 A | * 12/1998 | Gray et al. | 435/6 |
| 5,919,626 A | 7/1999 | Shi et al. | 435/6 |
| 5,925,552 A | 7/1999 | Keogh et al. | 435/6 |
| 5,965,362 A | 10/1999 | Pinkel et al. | 435/6 |
| 5,976,790 A | 11/1999 | Pinkel et al. | 435/6 |
| 6,040,138 A | * 3/2000 | Lockhart et al. | 435/6 |
| 6,048,695 A | * 4/2000 | Bradley et al. | 435/6 |
| 6,077,673 A | 6/2000 | Chenchik et al. | 435/6 |
| 6,136,962 A | 10/2000 | Shi et al. | 435/6 |
| 6,156,501 A | 12/2000 | McGall et al. | 435/6 |
| 6,159,695 A | 12/2000 | McGovern et al. | 435/6 |
| 6,426,183 B1 | * 7/2002 | Beattie | 435/6 |

FOREIGN PATENT DOCUMENTS

| | | |
|---|---|---|
| WO | 99/09218 | 2/1999 |
| WO | 99/13319 | 3/1999 |
| WO | WO 99 57323 | 11/1999 |

OTHER PUBLICATIONS

Kumar, et al., *Silanized nucleic acids: a general platform for DNA immobilization*, Nucleic Acids Res. (2000), vol. 28, No. 14, E71, II–VI, XP002188992.

Li, Minquian, et al., *Method for manufacturing DNA chips with large immobilized DNA fragments* Shanghai Inst. Of Atomic Nucleus. Chinese Academy of Sciences, Peop. R) Jan. 26, 2000. XP002189763.

Bertucci, et al., "Sensitivity issues in DNA array–based expression meaurements and performance of nylon microarrays for small samples", Hum Mol Genet 1999 Sep.: 8(9):1715–22.

Zhao, et al., "High–density cDMA filter analysis: a novel approach for large–scale, quantitative analysis of gene expression", Gene Apr. 24, 1995: 156(2):207–13.

Kern, et al., "Direct hybridization of large–insert genomic clones on high–density gridded cDNA filter arrays", Biotechniques Jul. 1997; 23(1):120–4.

DeRisi, et al., "Genomics and array technology", Current Opinion Oncology Jan. 1999: 11(1):76–9.

DR Walt, "Techview: molecular biology. Bead–based fiber–optic arrays." Science Jan. 21, 2000:287(5452):451–2.

Mark Schena, "Microarray Biochip Technology", Harcover Jan. 2000 Eaton Pub Co.; ISBN: 1881299376.

Yan, et al., "CpG Island Arrays: An Application toward Deciuphering Epigenetic Signatures of Breast Cancer", Clinical Cancer Research Apr. 2000: vol. 6, No. 4. 1432–1438.

Huang, et al., "Methylation profiling of CpG islands in human breast cancer cells", Human Molecular Genetics, 1999, vol. 8, No. 3m 459–470.

J. P. Issa, "CpG–Island Methylation in Aging and Cancer", Current Topics in Microbiology and Immunology, 249, pp. 101–118.

Pfeifer, et al., "Mutation Hotspots and DNA Methylation", Current Topics in Microbiology and Immunology, 249, pp. 1–19.

Eads, et al., "MethyLight: a high–throughput assay to measure DNA methylation", Nucleic Acids Research, 2000 vol. 28, No. 8 E32–00.

(Continued)

*Primary Examiner*—Jeffrey Fredman
*Assistant Examiner*—Suryaprabha Chunduru
(74) *Attorney, Agent, or Firm*—Sonia K. Guterman; Mintz, Levin, Cohn, Ferris, Glovsky and Pepeo, P.C.

(57) ABSTRACT

The invention provides biological molecules modified by reaction with a compound having the formula: $R_1$—X—$R_2$, wherein $R_1$ is a cyclic ether group or an amino group, $R_2$ is an alkoxysilane group and X is a moiety chemically suitable for linking the cyclic ether group or the amino group to the alkoxysilane group. The invention also provides arrays, or "biochips," comprising these modified biological molecules. Also provided are methods for making and using these compositions.

79 Claims, 5 Drawing Sheets

OTHER PUBLICATIONS

Pogribny, et al., "A Sensitive New Method for Rapid Detection of Abnormal Methylation Patterns in Global DNA and within CpG Islands", Biochemical and Biophysical Research Communications 262, 624–628 (1999).

Edward J. Oakeley, "DNA methylation analysis: a review of current methodologies", Pharmacology & Therapeutics, vol. 84, No. 3, Dec. 1999, pp. 389–400.

Robertston, et al., "DNA methylation: past, present and future directions" Carcinogenesis, vol. 21, No. 3, Mar. 2000, pp. 461–467.

Sapolsky, et al., "High–throughput polymorphism screening and genotyping with high–density oligonucleotide arrays", Genetic Analysis Biomolecular Engineering, vol. 14, Nos. 5–6, Feb. 1999.

Emerson, et al., LXIII Cold Spring Harbor Symposium on Quantitative Biology: Mechanisms of Transcription, Biochimica et Biophysica Acta 1423 (1998) R45–R51.

Kern, et al., "Direct Hybridization of Large–Insert Genomic Clones on High–Density Gridded cDNA Filter Arrays", BioTechniques 23:120–124, Jul. 1997.

Rice, et al., "Comparative Genomic Hybridization in Pediatric Acute Lymphoblastic Leukemia", Pediatric Hematology and Oncology, 17:141–147, 2000.

Kim, et al., "Putative Chromosomal Deletions on 9P, 9Q, and 22Q Occur Preferentially in Malignant Gastrointestinal Stromal Tumors", Int. J. Cancer: 85, 633–638 (2000).

Houdlsworth, et al., "Comparative Genomic Hybridization: An Overview", American Journal of Pathology, vol. 145, No. 6, Dec. 1994.

Wa el Fi–Rital, et al., "High–Resolution Deletion Mapping of Chromosome 14 in Stromal Tumors of the Gastrointestinal 14 in Stromal Tumors of the Gastrointestinal Tract Suggests Two Distinct Tumor Suppressor Loci", Genes, Chromosomes & Cancer 27:387–391 (2000).

David J. Stewart, "Making and Using DNA Microarrays: A Short Course at Cold Spring Harbor Laboratory", Genome Research, www.genomc.org.

Suzuki, et al., "Construction and evaluation of a porcine bacterial artifical chromosome library", Anim Genet Feb. 2000: 31(1): 8–12.

Schena, et al., "Quantitative monitoring of gene expression patterns with a complementary DNA microarray", Science Oct. 20, 1995: 270.

* cited by examiner

ARTICLES OF MANUFACTURE AND METHODS FOR ARRAY BASED ANALYSIS OF BIOLOGICAL MOLECULES

CROSS-REFERENCES TO RELATED APPLICATIONS

The present application is a Continuation-In-Part (CIP) of U.S. patent applications Ser. No. 09/546,085, filed on Apr. 10, 2000; which is a CIP of U.S. Ser. No. 09/071,876, filed on May 4, 1998, issued as U.S. Pat. No. 6,048,695, on Apr. 11, 2000. These aforementioned applications and patent are explicitly incorporated herein by reference in their entirety and for all purposes.

TECHNICAL FIELD

The present invention claims a closely related family of compounds, devices, and methods relating to techniques for immobilizing biological molecules, e.g., nucleic acids, to a solid support for the purpose of conducting scientific investigation or routine testing upon the bound molecule (e.g., nucleic acid) samples in areas such as genome-wide genetic mapping and gene expression studies, protein interaction studies, peptide interaction studies and small molecule interactions with larger macromolecules.

BACKGROUND

A large percentage of investigation in the biochemical arts is directed to studies involving nucleic acids, particularly deoxyribonucleic acid, or DNA. DNA is a water-soluble compound, that if left in solution (i.e., a water-based solution), is likely to degrade, through hydrolysis, and so forth. Obviously this frustrates any investigation involving DNA, and so therefore, accurate and reliable study involving DNA requires a method or device to ensure the integrity of DNA. To facilitate the study of DNA, it is often desirable to affix or immobilize the DNA on a solid surface, such as a smooth sheet of glass. Fixed in place in this manner, the DNA can be readily manipulated (i.e., reacted with other substances). If DNA is envisioned as a long strand, then immobilizing DNA means fixing one end of the strand to the solid support so that the remainder of the strand is unmodified and free to undergo further reaction depending upon the particular study. Indeed, this is a widely used method to conduct laboratory studies involving DNA.

Perhaps the major problem associated with immobilizing DNA on a solid support is exactly how to do it without altering the DNA (other than that relatively small portion that is actually bound to the solid support). This is a very difficult problem because whatever solid support is used must be essentially inert. That is, it must not react with the DNA, other than simply to immobilize it upon the solid support. Glass is a particularly suitable solid support, because it is inexpensive, and highly inert. At present, the current orthodoxy is that the solid support (e.g., a glass surface) must first be primed or derivatized so that it can bind one end of the DNA to the surface. Numerous techniques exist to do this.

Unfortunately, derivatizing the otherwise inert surface of glass creates problems that could confound the results of the laboratory study involving DNA. One problem is that derivatizing the glass surface creates a net positive electrostatic charge on the glass surface. Since DNA is (net) negatively charged, other DNA (or DNA used later in the study but not deliberately affixed to the glass surface) is prone to stick (by non-specific electrostatic attraction) to the glass surface. In other words, DNA "probes" which are single (rather than double) strands of DNA are often contacted with an array of DNA single strands affixed to a solid support. Since the probe has a known nucleotide sequence and since a particular single strand of DNA will bind preferentially to a complementary strand, the particular immobilized strand to which the probe reacts reveals the nucleotide sequence of the previously unknown immobilized strand. Yet simple experiments of this type (probe studies) are severely confounded by electrostatic sticking of the probe to the derivatized (hence electrostatically charged) glass surface. For instance, the probe is often radiolabeled so that its presence can be detected by an ordinary radiation detector. Thus, the location of the probe on the glass surface, as evidenced by the detector, reveals the chemical identity or sequence of the immobilized DNA strand at that particular location on the glass surface (which is known and designated in advance). Yet the radiation detector is unable to distinguish between probe that is chemically bound to a complementary strand of DNA affixed to the solid support, and probe that is simply electrostatically stuck to the glass surface (but not to a DNA strand).

Second, derivatized surfaces result in what shall be known as "spreading." Spreading occurs because the solid support surface becomes hydrophilic upon derivatization. As a result, when the DNA (desired to be immobilized upon the solid support) is contacted with the surface of the solid support, it spreads, rather than remaining in a discrete "spot," which it should ideally do, since whether the radioactive probe is detected in one spot or another determines whether the scientist infers that the probe reacted with this or that immobilized DNA. Spreading is a major constraint on array density (i.e., the number of different nucleic acid samples that can be arranged on a single solid support). Hence, any means to curtail spreading, and so increase array density, is highly desirable.

One very common substance used to prepare a glass surface to receive a nucleic acid sample is poly-L-lysine. See, e.g., DeRisi (1996) 14 Nature Genetics 457; Shalon (1996) 6 Genome Res. 639; and Schena (1995) 270 Science 467. Other types of pre-derivatized glass supports are commercially available (e.g., sialylated microscope slides). See, e.g., Schena (1996) 93 Proc. Natl. Acad. Sci. USA 10614.

Numerous other surface coatings have been disclosed. See, e.g., U.S. Pat. No. 5,630,932, discloses a coating for a probe (platinum) tip for use in scanning tunneling microscopy; numerous means are disclosed for coating the surface, notably, $Si(OCH_3)CH_2I$. U.S. Pat. No. 5,610,287, discloses coating a solid support with a salt or cationic detergent to non-covalently bond nucleic acids to the support. U.S. Pat. No. 5,024,933, discloses coating a solid support with an isolate of naturally occurring mussel adhesive protein. U.S. Pat. No. 4,937,188, discloses covalently bonding an enzyme to a solid support via molecular chain which acts as a substrate for the enzyme. U.S. Pat. No. 4,818,681, discloses coating a solid support with a nucleoside phosphate through the heterocyclic moiety of the nucleoside; the nucleic acid is then immobilized upon the solid support by enzymatic coupling. U.S. Pat. No. 4,806,631, discloses activating a nylon solid support by partially solvolyzing the amine groups (e.g., by treating with an alkylating group) on the nylon surface.

Another approach to this problem involves derivatizing both the solid support and the nucleic acid sought to be immobilized. See, e.g., U.S. Pat. No. 5,641,630, discloses coating a solid support with a complexing agent that binds to another complexing agent to which the nucleic acid sought to be bound is likewise bound. U.S. Pat. No. 5,554,744, discloses contacting a solid support with diisopropylcarbodiimide and an acid catalyst and a succinylated nucleoside to immobilize the nucleoside. U.S. Pat. No. 5,514,785, discloses coating a solid support with, preferably, primary and secondary amines, followed by activation of the nucleic acid using cyanuric chloride. U.S. Pat. No. 5,215,882, discloses modifying the nucleic acid sought to be immobilized with a primary amine or equivalent, followed by reaction of the modified nucleic acid with the solid support (the support must have free aldehyde groups) in the presence of a reducing agent.

Finally, a third approach to the problem of immobilizing nucleic acids to solid support material involves creating a novel solid support. See, e.g., U.S. Pat. Nos. 5,055,429, 5,008,220, 4,963,436, 4,826,790, and 4,826,789, disclose solid support material made from aluminosilicate material.

Due to the aforementioned shortcomings of derivatizing the (entire) glass surface prior to affixing the nucleic acid samples, several methods have been developed which involve synthesizing the nucleic acid samples directly to the solid support. See, e.g., Hacia (1996) 14 Nature Genetics 441 (1996); Lockhart (1996) 14 Nature Biotechnology 1675 (1996); Maskos (1992) 20 Nucleic Acids Res. 1679 (1992).

To reiterate: at present, the prevailing view in the biochemical arts is that, in order to effectively immobilize nucleic acids onto solid surfaces, the solid support must first be derivatized, or made chemically labile, so that the nucleic acid can then be reacted with solid support. In addition, epoxides are known mutagens; that is, they are known to damage nucleic acids, particularly DNA.

SUMMARY

This invention provides compositions and methods for affixing biological molecules to solid supports. It demonstrates that any biological molecule can be modified and affixed to an unmodified solid support. A skilled artisan will recognize the significance of first modifying a molecule to enhance its binding affinity by appropriate modifications; thus, this modified molecule can be immobilized to an unmodified solid surface to generate a fully functional array of molecules for a spectrum of specific applications.

In one aspect, the invention provides any biological molecule, e.g., DNA and nucleic acids more generally, that are modified such that they readily adhere to an unmodified or underivatized glass surface. In particular, in one aspect of the invention epoxide-modified nucleic acids, particularly DNA, are readily affixed to an unmodified solid support.

The invention provides a modified biological molecule comprising a biological molecule modified by reaction with a compound having the formula:

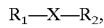

wherein $R_1$ is a cyclic ether group or an amino group, $R_2$ is an alkoxysilane group and X is a moiety chemically suitable for linking the cyclic ether group or the amino group to the alkoxysilane group. In one aspect, the $R_1$ cyclic ether is a compound comprising an epoxide group, such as an ethylene oxide, or equivalent. In alternative aspects, the cyclic ether is an oxirane group, or equivalent, or a compound comprising an aromatic hydrocarbon epoxide group.

In one aspect, the $R_1$ group reacts with the biological molecule such that the modified biological molecule is linked to the compound through $R_1$ group. The linkage, or association, of the $R_1$ group to the biological molecule can be such that the $R_1$ group is covalently or non-covalently bound to the biological molecule.

In alternative aspects, the biological molecule comprises a nucleic acid (e.g., a oligonucleotide), a lipid, a polysaccharide, a polypeptide (e.g., a peptide), or an analog or a mimetic thereof, or a combination thereof. The nucleic acid can comprise a DNA (e.g., a genomic DNA or a cDNA), an RNA (e.g., an mRNA, rRNA, and the like) or an analog or a mimetic thereof or a combination thereof. The nucleic acid can further comprise a telomeric structure or a chromatin structure.

In one aspect, the nucleic acid is attached to the compound by the $R_1$ group, i.e., the nucleic acid reacts with the $R_1$ group at its 5' end.

In one aspect, the cyclic ether is an epoxide group and the alkoxysilane is —Si(OCH$_3$)$_3$, —Si(OC$_2$H$_5$)$_3$, —Si(OCH$_3$)H$_2$, —Si(OCH$_3$)(CH$_3$)$_2$, or —Si(OCH)$_3$)$_2$ CH$_3$. In one aspect, the cyclic ether is an epoxide group and the compound is 3-glycidoxypropyltrimethoxysilane.

In one aspect, the $R_1$ group is a primary amino group. In one aspect, the $R_1$ group is an amino group and the alkoxysilane is selected from the group consisting of —Si(OCH$_3$)$_3$, —Si(OC$_2$H$_5$)$_3$ and

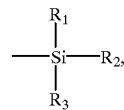

wherein $R_1$, $R_2$ and $R_3$ are selected from the group consisting of —H, —CH$_3$, —OCH$_3$, and —OC$_2$H$_3$, and provided that at least one of $R_1$, $R_2$ or $R_3$ is either —OCH$_3$ or —OC$_2$H$_3$.

In one aspect, the $R_1$ group is an amino group and the compound is 3-aminopropyltriethoxysilane.

The invention provides an article of manufacture comprising an arrayed plurality of biological molecules covalently bound to a surface, wherein, before attachment to the surface, the biological molecules are modified by reaction with a compound having the formula: $R_1$—X—$R_2$, wherein $R_1$ is a cyclic ether group or an amino group, $R_2$ is an alkoxysilane group and X is a moiety chemically suitable for linking the cyclic ether group or the amino group to the alkoxysilane group, and upon attachment to the surface the modified biological molecules are covalently bound to the surface; wherein each biological molecule is attached to the surface on at least one discrete and known location to form a cluster of substantially identical biological molecules. In alternative aspects of the article of manufacture the surface is a glass, a mica, a quartz, or a metal oxide surface. The metal oxide surface can be an alumina (Al$_2$O$_3$), a titania (TiO$_2$), a SnO$_2$, a RuO$_2$, or a PtO$_2$, or an equivalent thereof. The surface of the article of manufacture can comprise a polystyrene, a polyester, a polycarbonate, a polyethylene, a polypropylene or a nylon.

In one aspect, the modified biological molecules are covalently bound to the surface via the $R_2$ group.

On one aspect of the article of manufacture, the biological molecules can comprise a nucleic acid, a lipid, a polypeptide, a polysaccharide, or an analog or a mimetic thereof, or a combination thereof. In alternative aspects, the biological molecules are derived from a virus, a bacteria, a yeast, a plant, an insect, a mammal, such as a human or a mouse. The biological molecules can comprise nucleic acids or analogs or mimetics thereof. The nucleic acids can comprise DNA, RNA or analogs or mimetics thereof or a combination thereof. The nucleic acids can be oligonucleotides.

In one aspect of the article of manufacture, the nucleic acids react with the $R_1$ group at their 5' end.

In one aspect, the nucleic acids immobilized on the article of manufacture can comprise a plurality of fragments of a genomic nucleic acid. The biological molecule, e.g., a genomic nucleic acid or RNA, can be derived from a normal cell or an abnormal cell, such as a cell suspected of having a chromosomal defect or abnormality, e.g., a cancer or tumor cell. In alternative aspects, the genomic DNA is derived from a virus, a bacteria, a yeast, a plant, an insect, a mammal, such as a human or a mouse.

In one aspect of the article of manufacture, the fragments of nucleic acid, e.g., genomic nucleic acid, further comprise a cloning vehicle. The cloning vehicle can comprise a bacterial artificial chromosome (BAC). In alternative aspects, the cloning vehicle comprises a plasmid, a cosmid, a bacteriophage P1-derived vector (PAC), a yeast artificial chromosome (YAC) or a mammalian artificial chromosome (MAC).

In one aspect of the article of manufacture, the nucleic acid comprises a plurality of CpG island tags.

In one aspect of the article of manufacture, the fragments of genomic nucleic acid comprise sequences representing at least one substantially complete chromosome or at least one defined section of a chromosome. In one aspect, each genomic nucleic acid fragment has been mapped to a known location on a chromosome. In alternative aspects, the nucleic acid, e.g., the genomic nucleic acid fragments, have a size no more than about 1.5 megabase, no more than about 1.2 megabase, no more than about 1.0 megabase, and, no more than about 0.75 megabase in size.

In alternative aspects of the article of manufacture, each cluster of substantially identical biological molecules consists of between about 5 and about 400, or, between about 10 and about 200, or, between about 50 and 100, substantially identical copies of a biological molecule. The surface can consist of less than about 800, about 600, about 500, about 400, about 300, about 200 or about 100 clusters per square centimeter.

In alternative aspects of the article of manufacture, each cluster of substantially identical biological molecules is about 100 microns, about 50 microns, about 25 microns, about 15 microns or about 10 microns in diameter or smaller.

The invention provides an article of manufacture (e.g., array or biochip) comprising an array of cloned genomic nucleic acid fragments representing a defined subsection of or a substantially complete chromosome, wherein, before attachment to the surface, the cloned fragments are modified by reaction with a compound having the formula:

$R_1$—X—$R_2$, wherein $R_1$ is an epoxide group, $R_2$ is an alkoxysilane group and X is a moiety chemically suitable for linking the epoxide group and the alkoxysilane group, and the modified cloned fragments are covalently bound to the surface; wherein each array-bound cloned fragment has been mapped to a known location on a chromosome.

The invention provides a kit comprising an article of manufacture of the invention, as described herein, and printed matter, wherein the printed matter comprises instructions on hybridizing a sample of nucleic acid to an array-bound nucleic acid.

The invention provides a method for identifying a specific binding partner, comprising: (a) providing an article of manufacture comprising an arrayed plurality of biological molecules covalently bound to a surface, wherein, before attachment to the surface, the biological molecules are modified by reaction with a compound having the formula: $R_1$—X—$R_2$, wherein $R_1$ is an cyclic ether group or an amino group, $R_2$ is an alkoxysilane group and X is a moiety chemically suitable for linking the cyclic ether group or the amino group to the alkoxysilane group, and upon attachment the modified biological molecules are covalently bound to the surface, wherein each biological molecule is attached to the surface on at least one discrete and known location to form a cluster of identical biological molecules; (b) providing a sample of biological molecules; (c) contacting the sample of step (b) with the array-bound biological molecules as set forth in step (a) under conditions permissive for specific binding of a molecule in the sample of step (b) to an array-bound biological molecule; and, (d) screening for specific binding of a molecule in the sample of step (b) to an array-bound biological molecule, thereby identifying a specific binding partner. In one aspect, the method further comprises at least one wash step between the contacting of step (c) and the screening of step (d).

The invention provides a method for generating a molecular profile of a nucleic acid sample, comprising the following steps: (a) providing an article of manufacture comprising an array of biological molecules, wherein, before attachment to the surface, the biological molecules are modified by reaction with a compound having the formula: $R_1$—X—$R_2$, wherein $R_1$ is a cyclic ether group, $R_2$ is an alkoxysilane group and X is a moiety chemically suitable for linking the cyclic ether group and the alkoxysilane group, and the modified biological molecules are covalently bound to the surface; (b) providing a sample comprising a nucleic acid; and (c) contacting the nucleic acid with the array-bound biological molecules as set forth in step (a) under conditions, allowing binding of the sample nucleic acid to the array-bound biological molecules, and detecting binding of the sample nucleic acid to the array-bound biological molecules, thereby generating a molecular profile of the sample nucleic acid.

In one aspect of this method, the array-bound biological molecules comprise a nucleic acid, such as a DNA corresponding to, or derived from, a genomic DNA, or, a message. The binding can comprise hybridization of the sample nucleic acid to the array-bound nucleic acid. The array-bound nucleic acid can represent a section of at least one a chromosome or at least one substantially complete chromosome. The chromosome can be a viral, a bacterial, a yeast, a plant, an insect, or a mammalian, such as a human or a mouse, chromosome. In one aspect, the array-bound nucleic acids have been mapped to a known location on a chromosome.

In one aspect of this method, the molecular profile is a comparative genomic hybridization (CGH). The molecular profile can comprise detection of a genomic DNA amplification, a genomic DNA deletion, or a genomic DNA insertion. The molecular profile can comprise detection of a point mutation.

In one aspect of this method, the molecular profile is the identification of a single or multiple point mutations, such as a single-nucleotide polymorphism (SNP). In one aspect of this method, the detection of a point mutation can further comprise use of a primer extension assay.

In one aspect of this method, the modified nucleic acid of the invention, or the array-bound nucleic acids, comprise on or more CpG island tags. In one aspect, the molecular profile is generated by a differential methylation hybridization (DMH) reaction. The sample nucleic acids can comprise genomic DNA digested with at least one methylation-sensitive restriction endonuclease and the molecular profile comprises detection and mapping of hypermethylated regions of the genome. The methylation-sensitive restriction endonuclease can be selected from the group consisting of NotI, SmaI, SacII, EagI, MspI, HpaII and BssHII.

In one aspect of this method, the molecular profile comprises detection of transcriptionally active regions of a genome. In one aspect, the sample of nucleic acid can be derived from a nuclear run-off assay; this sample can be modified by the methods of the invention, and, in one aspect, these modified nucleic acids are immobilized onto an array as set forth in the invention.

In one aspect of this method, the molecular profile comprises an analysis of a chromatin structure. The modified nucleic acids of the invention, or the array-bound biological molecule, can comprise a chromatin structure.

In one aspect of this method, the molecular profile comprises an analysis of a telomeric structure. The molecular profile of a telomeric structure can comprise an analysis of telomeric erosion or telomeric addition. The modified nucleic acids of the invention, or the array-bound biological molecule (e.g., nucleic acid), can comprise one or more telomere structures.

The invention provides a method for making a modified biological molecule comprising (a) providing a biological molecule; (b) providing a compound having the formula: $R_1$—X—$R_2$, wherein $R_1$ is a cyclic ether group or an amino group, $R_2$ is an alkoxysilane group and X is a moiety chemically suitable for linking the cyclic ether group or the amino group to the alkoxysilane group; and (c) reacting the biological molecule with the compound, thereby modifying the biological molecule with the compound.

The invention provides a method for making an article of manufacture (e.g., array or biochip) comprising an arrayed plurality of biological molecules covalently bound to a surface comprising (a) providing a biological molecule; (b) providing a compound having the formula: $R_1$—X—$R_2$, wherein $R_1$ is a cyclic ether group or an amino group, $R_2$ is an alkoxysilane group and X is a moiety chemically suitable for linking the cyclic ether group or the amino group to the alkoxysilane group; (c) providing a surface comprising hydroxyl groups; (d) reacting the biological molecule with the compound, thereby modifying the biological molecule with the compound; and, (e) depositing a plurality of modified biological molecules on the surface as discrete clusters, wherein a modified biological molecule is attached to the surface on at least one discrete and known location to form at least one cluster of substantially identical biological molecules; the array comprises at least two, a plurality of, clusters.

In one aspect of the method for making an article of manufacture, the compound used to modify the biological molecule (e.g., a nucleic acid) is a 3-glycidoxypropyltrimethoxysilane. In one aspect, the biolog reaction with the 3-glycidoxypropyltrimethoxysilane is at a basic pH, thereby generating a modified nucleic acid. In this reaction, the pH can be above about pH 9.5. A 3-glycidoxypropyltrimethoxysilane modified nucleic ac surface at about a neutral pH.

In another aspect of the method for making an article of manufacture, the compound used to modify the biological molecule (e.g., a nucleic acid) is a 3-aminopropyltriethoxysilane. In one aspect, the biological m reaction with the 3-aminopropyltriethoxysilane is at about a neutral pH. This reaction can take place in the presence of sodium bisulfate, or equivalent. This modified nucleic acid can be deposited on an underivatized glass surface.

The modified biological molecules, such as a modified nucleic acid, of the invention, will adhere to a solid surface to allow subsequent biochemical investigations. Thus, in one aspect of the present invention, a modified biological molecule, such as a modified nucleic acid, comprises a biological molecule (e.g., a nucleic acid) covalently bound to moiety containing two crucial functional groups: a cyclic ether group and an alkoxysilane group. In accordance with other aspects of the present invention, methods for preparing the aforementioned modified biological molecules (e.g., nucleic acids) are claimed.

In another aspect, the invention provides a high-density microarray comprising a glass or other inert surface. This array, or "biochip," can be made by printing numerous highly discrete modified biological molecule (e.g., DNA) sample spots, or "clusters," upon the surface.

In another aspect, the invention provides a modified biological molecule (e.g., a nucleic acid) prepared from a biological molecule (e.g., a nucleic acid) and a halogenated silane, or equivalent.

In another aspect, the invention provides a modified nucleic acid prepared by reaction of a biological molecule (e.g., a nucleic acid) with a brominated moiety, followed by reaction with an aminated silane.

In another aspect, the invention provides a device that allows printing of the aforementioned high-density microarrays.

In another aspect, the invention provides modified silanes that allow the skilled artisan to modulate the electrostatic properties of the solid surface to optimize sample density and detection sensitivity.

The present invention possesses numerous advantages over the prior art. Many of the advantages derive from the fact that the solid surface, which is can be ordinary glass, remains highly chemically inert. Thus, the previously mentioned problems of probe (or other reactant) sticking to the glass as well as "spreading" are entirely eliminated. The ultimate result is, among other things, far higher detection sensitivity compared with state-of-the-art derivatized solid support.

In addition, the biological molecule (e.g., a nucleic acid) to be immobilized upon the solid support is readily derivatized. The reaction of the epoxide derivatives of the invention is simple to execute; it occurs under mild conditions, reaction rates are quick, and equilibrium is highly favorable. Moreover, the epoxide-modified biological molecules (e.g., nucleic acids) of the present invention are essentially permanently stable; thus they can be prepared (derivatized) and stored for later use (reaction with a non-derivatized surface).

The details of one or more aspects of the invention are set forth in the accompanying drawings and the description below. Other features, objects, and advantages of the invention will be apparent from the description and drawings, and from the claims.

All publications, GenBank Accession references (sequences), ATCC Deposits, patents and patent applications cited herein are hereby expressly incorporated by reference for all purposes.

DESCRIPTION OF DRAWINGS

Drawings are not necessary to scale. Certain features of the invention may be exaggerated in scale or shown in schematic form in the interest of clarity and conciseness. Like reference symbols in the various drawings indicate like elements.

DETAILED DESCRIPTION

Figure 1:
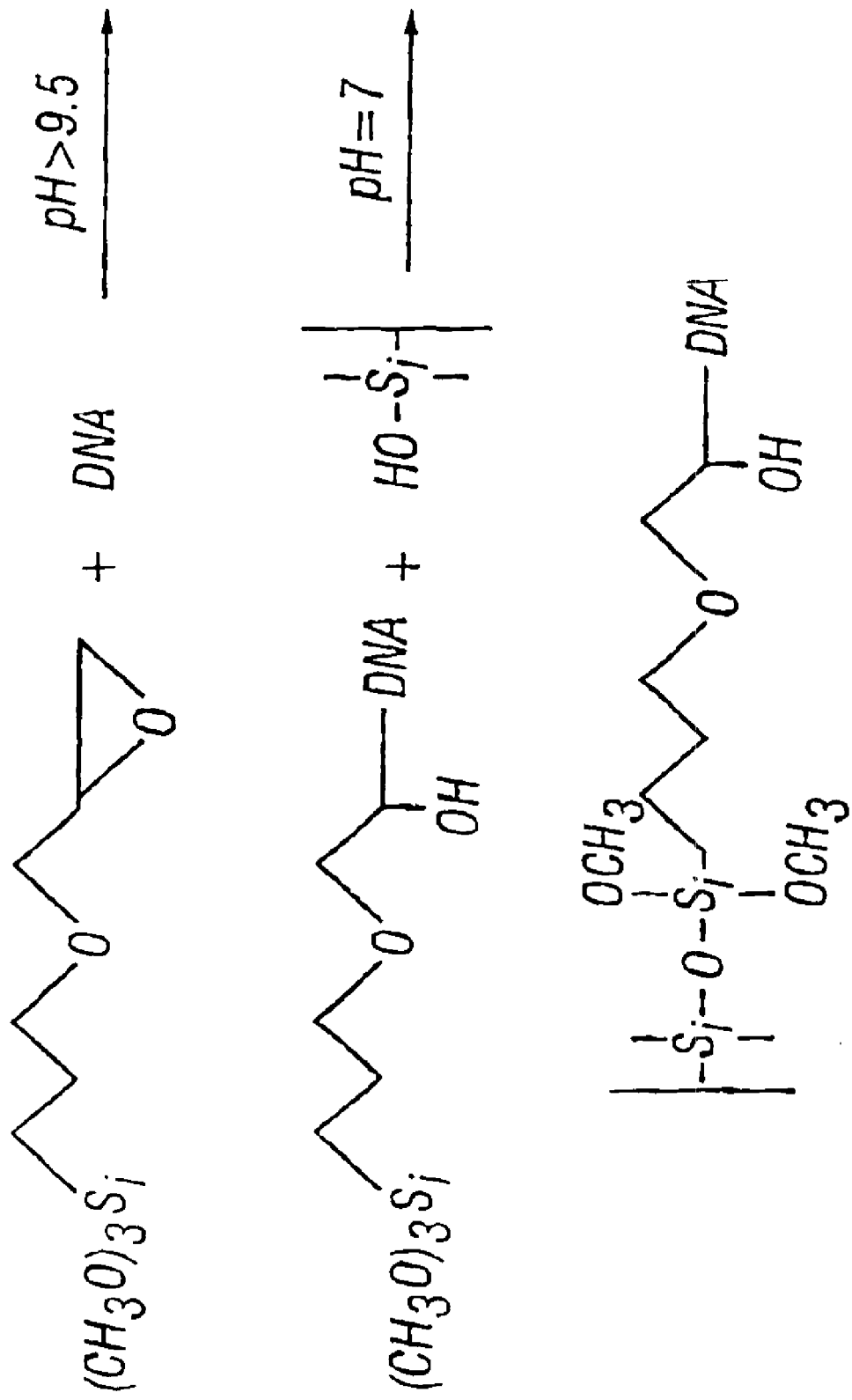
FIG. 1 depicts a coupling reaction of nucleic acid (in this instance DNA) with 3-glycidoxypropyltrimethoxysilane, followed by the reaction of the newly modified DNA and the solid support (in this instance a glass surface). The final reaction product, the immobilized DNA, is shown at bottom.

The invention provides modified biological molecules, such as polypeptides and nucleic acids, and articles of manufacture comprising arrays, with these modified biological molecules immobilized to the array surface. The invention also provides methods for making and using these compositions.

One aspect of the invention is chemical modification of the biological molecule (e.g., nucleic acid) sought to be immobilized. This chemically modified nucleic acid is then readily reacted to a solid support such as a glass surface, rendering the biological molecule (e.g., nucleic acid) immobilized. Again, this is in direct contradiction to the prior art, which teaches modification of the solid support, rather than the nucleic acid itself.

The modified the biological molecules (e.g., nucleic acids) of the present invention readily adhere to a variety of solid surfaces having reactive functional groups, e.g., hydroxyl groups. These include, though are not limited to: quartz glass, mica, alumina ($Al_2O_3$), titania ($TiO_2$), $SnO_2$, $RuO_2$, $PtO_2$, plastics such as the following polymer materials, polystyrene, polyester, polycarbonate, polyethylene, polypropylene, and nylon as well as numerous semi-conductive surfaces, such as numerous other metal oxide surfaces and equivalents.

In one family of aspects, the chemically modified biological molecules (e.g., nucleic acids) of the present invention are so modified with compounds having two crucial functionalities: a ring ether and an alkoxysilane group. The biological molecule (e.g., nucleic acid) reacts with the ring ether, then the newly modified biological molecules (e.g., nucleic acids) are contacted with the otherwise inert surface (e.g., glass), where the alkoxysilane group reacts with a hydroxyl-containing (e.g., hydroxyl derivatized) surface, e.g., Si—OH groups on the glass surface.

In another distinct family of aspects, the chemically modified biological molecules (e.g., nucleic acids) of the present invention are so modified with compounds having two crucial functionalities: an amino group and an alkoxysilane group. The biological molecules (e.g., nucleic acid) react with the amino group, then the newly modified biological molecules (e.g., nucleic acids) are contacted with the otherwise inert (e.g., glass) surface, where the alkoxysilane group reacts with a hydroxyl-containing (e.g., hydroxyl derivatized) surface, e.g., Si—OH groups on the glass surface.

In yet another distinct family of aspects, the biological molecules (e.g., nucleic acids) are modified by reaction with halogenated silane compounds.

In another set of aspects, the biological molecules (e.g., nucleic acids) are derivatized by a two-step process involving a final reaction with amine-containing silanes and brominated nucleic acids.

Other aspects are directed to preparing and optimizing high-density microarrays utilizing the modified biological molecules (e.g., nucleic acids) of the other aspects of the present invention.

Further aspects include compositions and methods of making and using that comprise any biological molecule or combinations of biological molecules. One skilled in the art realizes that nucleic acids, e.g., DNA or RNA, are only one of many biological compositions, e.g., biological polymers, that can be modified by the methods of the invention and used in the methods of the invention. A polymer refers to a molecule that has joined prefabricated units, e.g., monomers or compositions that can be of limited diversity, linked together, usually by identical mechanisms, e.g., a cellulose is a polymer is simple sugars or polysaccharides. Exemplary biological molecules include but are not limited to DNA, RNA, protein, peptides, lipids, saccharides, polysaccharides and mimetics and analogs thereof. Thus, a skilled artisan recognizes that any biological molecule, including those having a structure found in nature or a synthetic structure, including polymers, can be modified by the methods of the invention and affixed to a solid surface similar to the modified nucleic acids of the invention.

Another aspect of the invention is the modification of biological molecules. One type of modification is chemical cross-linking. It is well known in the art that bifunctional "crosslinking" reagents contain two reactive groups, thus providing a means of covalently crosslinking two target groups. The reactive groups in a chemical crosslinking reagent typically belong to the classes of functional groups, e.g., succinimidyl esters, maleimides and iodoacetamides. Bifunctional crosslinking reagents can be divided in homobifunctional, heterobifunctional and zero-length bifunctional crosslinking reagents. In homobifunctional crosslinking reagents, the reactive groups are identical. These reagents couple like functional groups, e.g., two thiols, two amines, two acids or two alcohols, and are predominantly used to form intramolecular crosslinks. In heterobifunctional crosslinking reagents, the reactive groups have dissimilar chemistry, allowing the formation of crosslinks between unlike functional groups. The "zero-length" crosslinking reagent forms a chemical bond between two groups without itself being incorporated into the product. For example, water-soluble cardodiimide (EDAC) is used to couple carboxylic acids to amines.

In addition to the traditional bifunctional crosslinking reagents, a noncovalent interaction between two molecules that has very slow dissociation kinetics can also function as a crosslink. For example, reactive derivatives of phospholipids can be used to link the liposomes or cell membranes to antibodies or enzymes. Biotinylation and haptenylation reagents can also be thought of as heterobifunctional crosslinking reagents because they comprise a chemically reactive group as well as a biotin or a hapten moiety that binds with high affinity to avidin or an anti-hapten antibody, respectively.

In contrast to chemical crosslinking reagents, photoreactive crosslinking reagents are available. The general scheme involves photoreactive crosslinking reagents that contain a chemically reactive group as well as a photoreactive group. These crosslinkers are first chemically reacted with one molecule and then this modified molecule is coupled to a second molecule using UV illumination. Depending on the reactive properties of the chemical and photoreactive groups, these crosslinkers can be used to couple like or unlike functional groups.

Other aspects are directed to preparing and optimizing high-density microarrays utilizing the modified molecules of the invention.

Definitions

Unless defined otherwise, all technical and scientific terms used herein have the meaning commonly understood by a person skilled in the art to which this invention belongs. As used herein, the following terms have the meanings ascribed to them unless specified otherwise.

The term "nucleic acid" as used herein refers to a deoxyribonucleotide (DNA) or ribonucleotide (RNA) in either single- or double-stranded form. The term encompasses nucleic acids containing known analogues of natural nucleotides. The term encompasses mixed oligonucleotides comprising an RNA portion bearing 2'-O-alkyl substituents conjugated to a DNA portion via a phosphodiester linkage, see, e.g., U.S. Pat. No. 5,013,830. The term also encompasses nucleic-acid-like structures with synthetic backbones. DNA backbone analogues provided by the invention include phosphodiester, phosphorothioate, phosphorodithioate, methylphosphonate, phosphoramidate, alkyl phosphotriester, sulfamate, 3'-thioacetal, methylene (methylimino), 3'-N-carbamate, morpholino carbamate, and peptide nucleic acids (PNAs); see Oligonucleotides and Analogues, a Practical Approach, edited by F. Eckstein, IRL Press at Oxford University Press (1991); Antisense Strategies, Annals of the New York Academy of Sciences, Volume 600, Eds. Baserga and Denhardt (NYAS 1992); Milligan (1993) J. Med. Chem. 36:1923–1937; Antisense Research and Applications (1993, CRC Press). PNAs contain non-ionic backbones, such as N-(2-aminoethyl) glycine units. Phosphorothioate linkages are described, e.g., by U.S. Pat. Nos. 6,031,092; 6,001,982; 5,684,148; see also, WO 97/03211; WO 96/39154; Mata (1997) Toxicol. Appl. Pharmacol. 144:189–197. Other synthetic backbones encompassed by the term include methyl-phosphonate linkages or alternating methylphosphonate and phosphodiester linkages (see, e.g., U.S. Pat. No. 5,962,674; Strauss-Soukup (1997) Biochemistry 36:8692–8698), and benzylphosphonate linkages (see, e.g., U.S. Pat. No. 5,532,226; Samstag (1996) Antisense Nucleic Acid Drug Dev 6:153–156). The term nucleic acid is used interchangeably with gene, DNA, RNA, cDNA, mRNA, oligonucleotide primer, probe and amplification product.

The terms "polypeptide," "protein," and "peptide" include compositions of the invention that also include "analogs," or "conservative variants" and "mimetics" or "peptidomimetics" with structures and activity that substantially correspond to the polypeptide from which the variant was derived, as discussed in detail, below.

The term "small molecule" means any synthetic small molecule, such as an organic molecule or a synthetic molecule, such as those generated by combinatorial chemistry methodologies. These small molecules can be synthesized using a variety of procedures and methodologies, which are well described in the scientific and patent literature, e.g., Organic Syntheses Collective Volumes, Gilman et al. (Eds) John Wiley & Sons, Inc., NY; Venuti (1989) *Pharm Res.* 6:867–873. Synthesis of small molecules, as with all other procedures associated with this invention, can be practiced in conjunction with any method or protocol known in the art. For example, preparation and screening of combinatorial chemical libraries are well known, see, e.g., U.S. Pat. Nos. 6,096,496; 6,075,166; 6,054,047; 6,004,617; 5,985,356; 5,980,839; 5,917,185; 5,767,238.

The terms "array" or "microarray" or "biochip" or "chip" as used herein is an article of manufacture, a device, comprising a plurality of immobilized target elements, each target element comprising a "cluster" or "biosite" or defined area comprising a biological molecule (e.g., a nucleic acid molecule or polypeptide, such as an antibody) immobilized to a solid surface, as discussed in further detail, below.

The term "sample of nucleic acid targets" or "sample of nucleic acid" as used herein refers to a sample comprising DNA or RNA, or nucleic acid representative of DNA or RNA isolated from a natural source, in a form suitable for hybridization (e.g., as a soluble aqueous solution) to another nucleic acid or polypeptide or combination thereof (e.g., immobilized probes). The nucleic acid may be isolated, cloned or amplified; it may be, e.g., genomic DNA, mRNA, or cDNA from substantially an entire genome, substantially all or part of a particular chromosome, or selected sequences (e.g. particular promoters, genes, amplification or restriction fragments, cDNA, etc.). The nucleic acid sample may be extracted from particular cells or tissues. The cell or tissue sample from which the nucleic acid sample is prepared is typically taken from a patient suspected of having a genetic defect or a genetically-linked pathology or condition, e.g., a cancer, associated with genomic nucleic acid base substitutions, amplifications, deletions and/or translocations. Methods of isolating cell and tissue samples are well known to those of skill in the art and include, but are not limited to, aspirations, tissue sections, needle biopsies, and the like. Frequently the sample will be a "clinical sample" which is a sample derived from a patient, including sections of tissues such as frozen sections or paraffin sections taken for histological purposes. The sample can also be derived from supernatants (of cells) or the cells themselves from cell cultures, cells from tissue culture and other media in which it may be desirable to detect chromosomal abnormalities or determine amplicon copy number. In some cases, the nucleic acids may be amplified using standard techniques such as PCR, prior to the hybridization. In alternative aspects, the target nucleic acid may be unlabeled, or labeled (as, e.g., described herein) so that its binding to the probe (e.g., oligonucleotide, or clone, immobilized on an array) can be detected. The probe an be produced from and collectively can be representative of a source of nucleic acids from one or more particular (pre-selected) portions of, e.g., a collection of polymerase chain reaction (PCR) amplification products, substantially an entire chromosome or a chromosome fragment, or substantially an entire genome, e.g., as a collection of clones, e.g., BACs, PACs, YACs, and the like (see below). The probe or genomic nucleic acid sample may be processed in some manner, e.g., by blocking or removal of repetitive nucleic acids or by enrichment with selected nucleic acids.

Generating and Manipulating Nucleic Acids

The invention provides modified nucleic acids, and articles of manufacture comprising arrays that include modified nucleic acid compositions and methods for making and using these arrays. The nucleic acid is modified by reaction with a compound having the formula: $R_1$—X—$R_2$, where $R_1$ is a cyclic ether group or an amino group, $R_2$ is an alkoxysilane group and X is a moiety chemically suitable for linking the cyclic ether group or the amino group to the alkoxysilane group. The modified nucleic acid or the immobilized nucleic acid on the array can be representative of genomic DNA, including defined parts of, or entire, chromosomes, or entire genomes. In several aspects, the arrays and methods of the invention are used in comparative genomic hybridization (CGH) reactions, including CGH reactions on arrays (see, e.g., U.S. Pat. Nos. 5,830,645; 5,976,790), see discussion below. The invention can be practiced in conjunction with any method or protocol or device known in the art, which are well described in the scientific and patent literature.

General Techniques

The nucleic acids used to practice this invention, whether RNA, cDNA, genomic DNA, vectors, viruses or hybrids thereof, may be isolated from a variety of sources, genetically engineered, amplified, and/or expressed/generated recombinantly (recombinant polypeptides can be modified or immobilized to arrays in accordance with the invention). Any recombinant expression system can be used, including bacterial, mammalian, yeast, insect or plant cell expression systems.

Alternatively, these nucleic acids can be synthesized in vitro by well-known chemical synthesis techniques, as described in, e.g., Carruthers (1982) Cold Spring Harbor Symp. Quant. Biol. 47:411–418; Adams (1983) J. Am. Chem. Soc. 105:661; Belousov (1997) Nucleic Acids Res. 25:3440–3444; Frenkel (1995) Free Radic. Biol. Med. 19:373–380; Blommers (1994) Biochemistry 33:7886–7896; Narang (1979) Meth. Enzymol. 68:90; Brown (1979) Meth. Enzymol. 68:109; Beaucage (1981) Tetra. Lett. 22:1859; U.S. Pat. No. 4,458,066. Double stranded DNA fragments may then be obtained either by synthesizing the complementary strand and annealing the strands together under appropriate conditions, or by adding the complementary strand using DNA polymerase with a primer sequence.

Techniques for the manipulation of nucleic acids, such as, e.g., subcloning, labeling probes (e.g., random-primer labeling using Klenow polymerase, nick translation, amplification), sequencing, hybridization and the like are well described in the scientific and patent literature, see, e.g., Sambrook, ed., MOLECULAR CLONING: A LABORATORY MANUAL (2ND ED.), Vols. 1–3, Cold Spring Harbor Laboratory, (1989); CURRENT PROTOCOLS IN MOLECULAR BIOLOGY, Ausubel, ed. John Wiley & Sons, Inc., New York (1997); LABORATORY TECHNIQUES IN BIOCHEMISTRY AND MOLECULAR BIOLOGY: HYBRIDIZATION WITH NUCLEIC ACID PROBES, Part I. Theory and Nucleic Acid Preparation, Tijssen, ed. Elsevier, N.Y. (1993).

Another useful means of obtaining and manipulating nucleic acids used in the compositions and methods of the invention is to clone from genomic samples, and, if necessary, screen and re-clone inserts isolated (or amplified) from, e.g., genomic clones or cDNA clones or other sources of complete genomic DNA. Sources of genomic nucleic acid used in the methods and compositions of the invention include genomic or cDNA libraries contained in, or comprised entirely of, e.g., mammalian artificial chromosomes (see, e.g., Ascenzioni (1997) Cancer Lett. 118:135–142; U.S. Pat. Nos. 5,721,118; 6,025,155) (including human artificial chromosomes, see, e.g., Warburton (1997) Nature 386:553–555; Roush (1997) Science 276:38–39; Rosenfeld (1997) Nat. Genet. 15:333–335); yeast artificial chromosomes (YAC); bacterial artificial chromosomes (BAC); P1 artificial chromosomes (see, e.g., Woon (1998) Genomics 50:306–316; Boren (1996) Genome Res. 6:1123–1130); PACs (a bacteriophage P1-derived vector, see, e.g., Ioannou (1994) Nature Genet. 6:84–89; Reid (1997) Genomics 43:366–375; Nothwang (1997) Genomics 41:370–378; Kern (1997) Biotechniques 23:120–124); cosmids, plasmids or cDNAs.

Amplification of Nucleic Acids

Amplification using oligonucleotide primers can be used to generate nucleic acids used in the compositions and methods of the invention, to detect or measure levels of test or control samples hybridized to an array, and the like. The skilled artisan can select and design suitable oligonucleotide amplification primers. Amplification methods are also well known in the art, and include, e.g., polymerase chain reaction, PCR (PCR PROTOCOLS, A GUIDE TO METHODS AND APPLICATIONS, ed. Innis, Academic Press, N.Y. (1990) and PCR STRATEGIES (1995), ed. Innis, Academic Press, Inc., N.Y., ligase chain reaction (LCR) (see, e.g., Wu (1989) Genomics 4:560; Landegren (1988) Science 241:1077; Barringer (1990) Gene 89:117); transcription amplification (see, e.g., Kwoh (1989) Proc. Natl. Acad. Sci. USA 86:1173); and, self-sustained sequence replication (see, e.g., Guatelli (1990) Proc. Natl. Acad. Sci. USA 87:1874); Q Beta replicase amplification (see, e.g., Smith (1997) J. Clin. Microbiol. 35:1477–1491), automated Q-beta replicase amplification assay (see, e.g., Burg (1996) Mol. Cell. Probes 10:257–271) and other RNA polymerase mediated techniques (e.g., NASBA, Cangene, Mississauga, Ontario); see also Berger (1987) Methods Enzymol. 152:307–316; Sambrook; Ausubel; U.S. Pat. Nos. 4,683,195 and 4,683,202; Sooknanan (1995) Biotechnology 13:563–564.

Polypeptides

The invention is directed to modified polypeptides and articles of manufacture comprising arrays with immobilized polypeptides, peptides and peptidomimetics. The polypeptide is modified by reaction with a compound having the formula: $R_1$—X—$R_2$, where $R_1$ is a cyclic ether group or an amino group, $R_2$ is an alkoxysilane group and X is a moiety chemically suitable for linking the cyclic ether group or the amino group to the alkoxysilane group. As noted above, the terms "polypeptide," "protein," and "peptide," used to practice the invention, include compositions of the invention that also include "analogs," or "conservative variants" and "mimetics" or "peptidomimetics." The terms "mimetic" and "peptidomimetic" refer to a synthetic chemical compounds. The mimetic can be either entirely composed of synthetic, non-natural analogues of amino acids, or, is a chimeric molecule of partly natural peptide amino acids and partly non-natural analogs of amino acids. The mimetic can also incorporate any amount of natural amino acid conservative substitutions as long as such substitutions also do not substantially alter the mimetics' structure and/or activity. Polypeptide mimetic compositions can contain any combination of non-natural structural components, which are typically from three structural groups: a) residue linkage groups other than the natural amide bond ("peptide bond")

linkages; b) non-natural residues in place of naturally occurring amino acid residues; or c) residues which induce secondary structural mimicry, i.e., to induce or stabilize a secondary structure, e.g., a beta turn, gamma turn, beta sheet, alpha helix conformation, and the like. A polypeptide can be characterized as a mimetic when all or some of its residues are joined by chemical means other than natural peptide bonds. Individual peptidomimetic residues can be joined by peptide bonds, other chemical bonds or coupling means, such as, e.g., glutaraldehyde, N-hydroxysuccinimide esters, bifunctional maleimides, N,N'-dicyclohexylcarbodiimide (DCC) or N,N'-diisopropylcarbodiimide (DIC). Linking groups that can be an alternative to the traditional amide bond ("peptide bond") linkages include, e.g., ketomethylene (e.g., —C(=O)—CH$_2$— for —C(=O)—NH—), aminomethylene (CH$_2$—NH), ethylene, olefin (CH=CH), ether (CH$_2$—O), thioether (CH$_2$—S), tetrazole (CN$_4$—), thiazole, retroamide, thioamide, or ester (see, e.g., Spatola (1983) in Chemistry and Biochemistry of Amino Acids, Peptides and Proteins, Vol. 7, pp 267–357, "Peptide Backbone Modifications," Marcell Dekker, NY). A polypeptide can also be characterized as a mimetic by containing all or some non-natural residues in place of naturally occurring amino acid residues; non-natural residues are well described in the scientific and patent literature. The skilled artisan will recognize that individual synthetic residues and polypeptides incorporating mimetics can be synthesized using a variety of procedures and methodologies, which are well described in the scientific and patent literature, e.g., Organic Syntheses Collective Volumes, Gilman, et al., supra. Polypeptides incorporating mimetics can also be made using solid phase synthetic procedures, as described, e.g., by U.S. Pat. No. 5,422,426. Peptides and peptide mimetics can also be synthesized using combinatorial methodologies. Various techniques for generation of peptide and peptidomimetic libraries are well known, and include, e.g., multipin, tea bag, and split-couple-mix techniques; see, e.g., al-Obeidi (1998) Mol. Biotechnol. 9:205–223; Hruby (1997) Curr. Opin. Chem. Biol. 1:114–119; Ostergaard (1997) Mol. Divers. 3:17–27; Ostresh (1996) Methods Enzymol. 267:220–234. Modified polypeptide and peptides can be further produced by chemical modification methods, see, e.g., Belousov (1997) Nucleic Acids Res. 25:3440–3444; Frenkel (1995) Free Radic. Biol. Med. 19:373–380; Blommers (1994) Biochemistry 33:7886–7896. These peptides can also be synthesized, whole or in part, using chemical methods well known in the art (see e.g., Caruthers (1980) Nucleic Acids Res. Symp. Ser. 215–223; Horn (1980) Nucleic Acids Res. Symp. Ser. 225–232; Banga, A. K., Therapeutic Peptides and Proteins, Formulation, Processing and Delivery Systems (1995) Technomic Publishing Co., Lancaster, Pa. Peptide synthesis can be performed using various solid-phase techniques (see e.g., Roberge (1995) Science 269:202; Merrifield (1997) Methods Enzymol. 289:3–13) and automated synthesis may be used.

Arrays, or "BioChips"

The invention provides "arrays" or "microarrays" or "biochips" or "chip" comprising the modified biological molecules of the invention, including the modified nucleic acids and polypeptides of the invention. Arrays are generically a plurality of target elements immobilized onto the surface of the array as defined "clusters," or "biosites," each target element comprising a one or more biological molecules (e.g., nucleic acids or polypeptides) immobilized a solid surface for association (e.g., specific binding or hybridization) to a sample. The immobilized nucleic acids can contain sequences from specific messages (e.g., as cDNA libraries) or genes (e.g., genomic libraries), including a human genome. Other target elements can contain reference sequences and the like. The biological molecules of the arrays may be arranged on the solid surface at different sizes and different densities. The densities of the biological molecules in a cluster and the number of clusters on the array will depend upon a number of factors, such as the nature of the label, the solid support, and the like. Each cluster/biosite may comprise substantially the same biological molecule (e.g., nucleic acid or polypeptide), or, a mixture of biological molecules (e.g., nucleic acids of different lengths and/or sequences). Thus, for example, a cluster/biosite may contain more than one copy of a cloned piece of DNA, and each copy may be broken into fragments of different lengths. The surface onto which the modified biological molecules of the invention are immobilized can include nitrocellulose, glass, quartz, fused silica, plastics and the like, as discussed further, below. The compositions and methods of the invention can incorporate in whole or in part designs of arrays, and associated components and methods, as described, e.g., in U.S. Pat. Nos. 6,197,503; 6,174,684; 6,156,501; 6,093,370; 6,087,112; 6,087,103; 6,087,102; 6,083,697; 6,080,585; 6,054,270; 6,048,695; 6,045,996; 6,022,963; 6,013,440; 5,959,098; 5,856,174; 5,843,655; 5,837,832; 5,770,456; 5,723,320; 5,700,637; 5,695,940; 5,556,752; 5,143,854; see also, e.g., WO 99/51773; WO 99/09217; WO 97/46313; WO 96/17958; WO 89/10977; see also, e.g., Johnston (1998) Curr. Biol. 8:R171–R174; Schummer (1997) Biotechniques 23:1087–1092; Kern (1997) Biotechniques 23:120–124; Solinas-Toldo (1997) Genes, Chromosomes & Cancer 20:399–407; Bowtell (1999) Nature Genetics Supp. 21:25–32; Epstein (2000) Current Opinion in Biotech. 11:36–41; Mendoza (1999 Biotechniques 27: 778–788; Lueking (1999) Anal. Biochem. 270:103–111; Davies (1999) Biotechniques 27:1258–1261.

Substrate Surfaces

The articles of manufacture of the invention comprising arrays can have substrate surfaces of a rigid, semi-rigid or flexible material. The substrate surface can be flat or planar, be shaped as wells, raised regions, etched trenches, pores, beads, filaments, or the like. Substrates can be of any material upon which a "capture probe" can be directly or indirectly bound. For example, suitable materials can include paper, glass (see, e.g., U.S. Pat. No. 5,843,767), ceramics, quartz or other crystalline substrates (e.g. gallium arsenide), metals, metalloids, polacryloylmorpholide, various plastics and plastic copolymers, Nylon™, Teflon™, polyethylene, polypropylene, poly(4-methylbutene), polystyrene, polystyrene/latex, polymethacrylate, poly (ethylene terephthalate), rayon, nylon, poly(vinyl butyrate), polyvinylidene difluoride (PVDF) (see, e.g., U.S. Pat. No. 6,024,872), silicones (see, e.g., U.S. Pat. No. 6,096,817), polyformaldehyde (see, e.g., U.S. Pat. Nos. 4,355,153; 4,652,613), cellulose (see, e.g., U.S. Pat. No. 5,068,269), cellulose acetate (see, e.g., U.S. Pat. No. 6,048,457), nitrocellulose, various membranes and gels (e.g., silica aerogels, see, e.g., U.S. Pat. No. 5,795,557), paramagnetic or superparamagnetic microparticles (see, e.g., U.S. Pat. No. 5,939,261) and the like. Reactive functional groups can be, e.g., hydroxyl, carboxyl, amino groups or the like. Silane (e.g., mono- and dihydroxyalkylsilanes, aminoalkyltrialkoxysilanes, 3-aminopropyl-triethoxysilane, 3-aminopropyltrimethoxysilane) can provide a hydroxyl functional group for reaction with an amine functional group.

Generating Molecular Profiles of Sample Nucleic Acids

The invention provides compositions and methods for generating a molecular profile of a nucleic acid sample, such as a sample of genomic DNA or a cDNA library. The invention provides articles of manufacture and methods for contacting array-bound nucleic acids with a sample containing nucleic acids and detecting the binding of the sample nucleic acids to the array, thereby generating a molecular profile of the sample nucleic acid. In alternative aspects of the methods of the invention, the molecular profile can be a comparative genomic hybridization (CGH) reaction; detection of a genomic DNA amplification, a genomic DNA deletion, or a genomic DNA insertion; detection of a point mutation, such as identification of a single-nucleotide polymorphism (SNP); differential methylation hybridization (DMH), where the array-bound nucleic acids are CpG island tags; detection of transcriptionally active regions of a genome (using, e.g., nuclear run-off assays); analysis of a chromatin structure; and analysis of a telomeric structure (such as telomeric erosion or telomeric addition). All of these procedures are well known in the art, and any molecular biology procedure or analysis, can be performed using the modified biological molecules or arrays of the invention.

Comparative Genomic Hybridization (CGH)

In one aspect, the arrays and methods of the invention are used in comparative genomic hybridization (CGH) reactions. CGH is a molecular cytogenetics approach that can be used to detect regions in a genome undergoing quantitative changes, i.e. gains or losses of copy numbers. Analysis of genomes of tumor cells can detect a region or regions of anomaly under going gains and/or losses. Differential expression of hundreds of genes can be analyzed using a cDNA array, thus facilitating characterization of gene expression in normal and diseased tissues. Generating a molecular profile of a nucleic acid sample by comparative genomic hybridization using methods and arrays of the invention can be practiced with methods and compositions known in the art, see, e.g., U.S. Pat. Nos. 6,197,501; 6,159,685; 5,976,790; 5,965,362; 5,856,097; 5,830,645; 5,721,098; 5,665,549; 5,635,351; and, Diago (2001) American J. of Pathol. May;158(5):1623–1631; Theillet (2001) Bull. Cancer 88:261–268; Werner (2001) Pharmacogenomics 2:25–36; Jain (2000) Pharmacogenomics 1:289–307.

Detection of Single-nucleotide Polymorphisms (SNPs)

In one aspect, the arrays and methods of the invention are used to detect point mutations, such as single-nucleotide polymorphisms (SNPs). Arrays can be used for high-throughput genotyping approaches for pharmacogenomics, where numerous individuals are studied with thousands of SNP markers. SNP mapping has accelerated complex disease gene localization; detection of multiple SNPs associated with a disease in a relatively small linkage disequilibrium region can narrow the linkage region for that disease, and, identification of susceptibility genes will enable a better understanding of the mechanisms of the disease processes and will facilitate the discovery of new and more efficacious medicines. Generating a molecular profile of a nucleic acid sample by the analysis and detection of SNPs using methods and arrays of the invention can be practiced with methods and compositions known in the art, see, e.g., U.S. Pat. Nos. 6,221,592; 6,110,709; 6,074,831; 6,015,888; and, Kwok (2000) Pharmacogenomics 1:95–100; Riley (2000) Pharmacogenomics 1:39–47; Kokoris (2000) Mol. Diagn. 5:329–340; Shi (2001) Clin. Chem. 47:164–172; Fan (2000) Genome Res. 10:853–860; Ianonne (2000) Cytometry 39:131–140; Cai (2000) Genomics.66:135–143; Chen (2000) Genome Res. 10:549–557; Syvanen (1999) Hum. Mutat. 13:1–10; Pastinen (1997) Genome Res. 7:606–614.

Differential Methylation Hybridization (DMH)

The arrays and methods of the invention are used in differential methylation hybridization (DMH), including, for example, CpG island analysis. In one aspect, the array-bound nucleic acids comprise CpG island tags. In one aspect, the methods and arrays of the invention are used to identify, analyze and map hypermethylated or hypomethylated regions of the genome. In one aspect, the sample nucleic acids can comprise genomic DNA digested with at least one methylation-sensitive restriction endonuclease and the molecular profile comprises detection and mapping of hypermethylated (or hypomethylated) regions of the genome. Any methylation-sensitive restriction endonuclease or equivalent endonuclease enzyme can be used, including, for example, NotI, SmaI, SacII, EagI, MspI, HpaII, Sau3AI and BssHII. In one aspect of the methods of the invention, both a methylation-sensitive enzyme and its methylation insensitive isoschizomer is used; see, e.g., Robinson (2000) Chromosome Res. 8:635–643; described use of the methylation-sensitive enzyme HpaII and its methylation insensitive isoschizomer MspI. Windhofer (2000) Curr. Genet. 37:194–199, described digestion of genomic DNA with the methylation-sensitive endonuclease Sau3AI and the methylation-insensitive endonuclease NdeII. See also, e.g., Muller (2001) J. Biol. Chem. 276:14271–14278; Memisoglu (2000) J. Bacteriol. 182:2104–2112; Roth (2000) Biol. Chem. 381:269–272.

DNA methylation, or the covalent addition of a methyl group to cytosine within the context of the CpG dinucleotide, has profound effects on the mammalian genome. These effects include transcriptional repression via inhibition of transcription factor binding or the recruitment of methyl-binding proteins and their associated chromatin remodeling factors, X chromosome inactivation, imprinting and the suppression of parasitic DNA sequences. DNA methylation is also essential for proper embryonic development, DNA repair and genome stability. For example, DNA demethylation influence on chromosome stability is modulated by a sequence-specific chromatin structure (the invention also provides modified biological molecules and arrays comprising chromatin structures) (see, e.g., Vilain (2000) Cytogenet. Cell. Genet. 90:93–101).

Normal methylation patterns are frequently disrupted in tumor cells with global hypomethylation accompanying region-specific hypermethylation. When these hypermethylation events occur within the promoter of a tumor suppressor gene, they will silence the gene and provide the cell with a growth advantage in a manner akin to deletions or mutations. For example, the Rb tumor suppressor pathway is frequently disrupted by methylation-dependent silencing of the p16INK4A gene and stimulation of Rb degradation by a proteosomal subunit (see, e.g., Buendia (2000) Semin. Cancer Biol. 10: 185–200). Reversal of abnormalities in DNA methylation may therefore restore the tumor-suppressive function of these genes and provide a novel approach to cancer therapy (see, e.g., Santini (2001) Ann. Intern. Med. 3;134(7):573–586. The transcriptional silencing of selected genes by DNA methylation plays a crucial role in the development and progression of human gastrointestinal malignancies (see, e.g., Toyota (2000) J. Gastroenterol. 35:727–734). Generating a molecular profile of a nucleic acid sample by the analysis of differential methylation and CpG islands using methods and arrays of the invention can be practiced with methods and compositions known in the art, see, also, U.S. Pat. Nos. 6,214,556; 6,180,344; 5,851,762; and, WO0127317, WO9928498; WO0044934; and WO1999DE03747 19991119.

Analysis of Telomeric Structure

The arrays and methods of the invention are used in the analysis of a telomeric structure, such as telomeric erosion or telomeric addition. The maintenance of telomeres, which are specialized nucleoprotein structures, is essential for chromosome stability. Without new synthesis of telomeres at chromosome ends the chromosomes shorten with progressive cell division. This eventually triggers either replicative senescence or apoptosis when telomere length becomes critically short. The regulation of telomerase activity in human cells plays a significant role in the development of cancer (telomerase is the enzyme that synthesizes the telomere ends of linear eukaryotic chromosomes). Telomerase is tightly repressed in the vast majority of normal human somatic cells, but becomes activated during cellular immortalization and in cancers. Thus, telomerase assays are useful for cancer detection and diagnosis (see, e.g., Hahn (2001) Ann Med 33:123–129; Meyerson (2000) J. Clin. Oncol. 18:2626–2634; Meyerson (1998) Toxicol. Lett. 102–103:41-5). Using the array-based telomeric structures of the invention will accelerate understanding of telomerase biology and lead to clinically relevant telomerase-based therapies. Generating a molecular profile of a nucleic acid sample by the analysis of telomeric structures using methods and arrays of the invention can be practiced with methods and compositions known in the art, see, e.g., U.S. Pat. Nos. 6,221,590; 6,221,584; 6,022,709; 6,007,989; 6,004,939; 5,972,605; 5,871,926; 5,834,193; 5,830,644; 5,695,932; 5,645,986.

Analysis of Chromatin Structure

The arrays and methods of the invention are used in the analysis of chromatin structure, including chromatin condensation, chromatin decondensation, histone phosphorylation, histone acylation, and the like (see, e.g., Guo (2000) Cancer Res. 60:5667–5672; Mahlknecht (2000) Mol. Med. 6:623–644). Chromatin structure remodeling occurs in certain cancers (see, e.g., Giamarchi (2000) Adv. Exp. Med. Biol. 480:155–161). Chromatin structure affects nuclear processes that utilize DNA as a substrate, e.g., transcription, replication, DNA repair, and DNA organization within the nucleus. Chromatin structure analysis is useful in fertility assessment; for example, sperm with decondensed chromatin are infertile. DNA damage in patients with untreated cancer can be measured using a sperm chromatin structure assay (see, e.g., Kobayashi (2001) Fertil. Steril. 75:469–475). Generating a molecular profile of a nucleic acid sample by the analysis of chromatin structure using the methods and arrays of the invention can be practiced with methods and compositions known in the art, see, e.g., U.S. Pat. Nos. 6,204,064; 6,187,749; 6,097,485; 5,972,608; 5,919,621; 5,470,709; and, Dreyer (2000) Anal. Cell Pathol. 20:141–150; Hong (2001) Acta Cytol. 45:163–168; Evenson (1991) Reprod. Toxicol. 5:115–125.

Nuclear Run-off Assay

The arrays and methods of the invention are used in the detection and analysis of transcriptionally active regions of nucleic acid, e.g., transcriptionally active regions of a genome. In one aspect, a sample of nucleic acid can be derived from a nuclear run-off assay and detected and analyzed by the compositions and methods of the invention. In another aspect, nuclear run-off samples are modified by the methods of the invention. In one aspect, these modified nucleic acids are immobilized onto an array as set forth in the invention.

Generating a molecular profile of a nucleic acid sample by the detection and analysis of transcriptionally active regions of nucleic acid by, e.g., nuclear run-off assays, using the methods and arrays of the invention can be practiced with methods and compositions known in the art, see, e.g., U.S. Pat. Nos. 6,200,960; 6,184,032; 6,175,060; 6,159,751; 6,022,694; 5,994,523; and, Delany (2001) Methods Mol. Biol. 151:321–333; Srivastava (1998) Methods Mol. Biol. 86:201–207; Greene (1994) J. Biochem. Biophys. Methods 29:179–187; Srivastava (1994) Methods Mol. Biol. 31:281–288.

It will be readily apparent to one skilled in the art that various substitutions and modifications may be made to the invention disclosed herein without departing from the scope and spirit of the invention. It is understood that the examples and aspects described herein are for illustrative purposes only and that various modifications or changes in light thereof will be suggested to persons skilled in the art and are to be included within the spirit and purview of this application and scope of the appended claims.

EXAMPLES

The following example is offered to illustrate, but not to limit the claimed invention.

Example 1

Preparation of Modified Nucleic Acid Using 3-glycidoxypropyl-trimethoxysilane

The following example describes making and using one aspect of modified nucleic acid of the present invention. The purpose of the chemical modification is to enable the nucleic acid to be readily affixed to an underivatized solid surface. In this example, the nucleic acid—preferably DNA—is modified by reaction with 3-glycidoxypropyl-trimethoxysilane (GPTS), according to FIG. 1. GPTS has in fact been previously used to derivatize a glass surface upon which (unmodified) DNA samples are then contacted and immobilized. Yet the use of GPTS is for the opposite purpose: to modify the DNA for subsequent attachment to an underivatized glass surface, has not been previously disclosed nor suggested. Moreover, GPTS—since it contains an epoxide group—is known to damage DNA in vivo. For these reasons, its use to derivatize DNA is actually discouraged by the prior art.

Schematically, affixing the nucleic acid to the solid support consists essentially of two steps. In the first, the nucleic acid reacts with the epoxide end of the GPTS molecule; in the second step, the glass surface reacts with the other end, or the silane end of the GPTS-modified nucleic acid, thereby affixing the nucleic acid onto an underivatized glass surface. The entire reaction is rapid, is characterized by a favorable equilibrium, and occurs under very mild conditions using a minimum of inexpensive reagents. Though there quite obviously are numerous ways to carry out either step of the reaction, the preferred method is shown in this and the following example.

As depicted in FIG. 1, a chemical compound having a cyclic or ring ether and an alkoxysilane—in this instance ethylene oxide and trimethyloxysilane, respectively—comprise the two ends of the compound; the two ends are connected by a four-carbon ether linkage. The compound shown is 3-glycidoxypropyltrimethoxysilane or GPTS. In the first step, DNA is reacted with GPTS at basic pH, preferably above 9.5, to form the modified DNA. The modified DNA is then reacted with an underivatized glass (or other silanol-containing) surface at neutral pH, thus immobilizing the DNA onto the glass surface. In the first step, the ring ether functionality reacts with the DNA. Again, the ring ether need not be ethylene oxide, as it is in GPTS, although the small ring is preferred to increase reactivity of the ether functionality, which is relatively unreactive.

The first reaction, leading to the derivatized DNA, is a ring-opening reaction likely involving carbon 5 of the ribose ring of the DNA. This derivatized DNA is unusually stable and can be stored for long periods of time prior to actual use. The second reaction, immobilizing the derivatized DNA onto the glass surface, is a simple substitution reaction creating an Si—O—Si linkage in the glass surface, and removing one of the alkoxy groups from the GPTS molecule.

Example 2

Preparation of Modified Nucleic Acid Using 3-aminopropyl-triethoxysilane

The following example describes making and using another aspect of modified nucleic acids of the present invention. The purpose of the chemical modification is to enable the nucleic acid to be readily affixed to an underivatized solid surface. In this example, the nucleic acid, preferably DNA, is modified by reaction with 3-aminopropyl-trimethoxysilane, according to FIG. 2. As in example 1, affixing the nucleic acid to the solid support consists essentially of two steps. In the first, the nucleic acid reacts with the amino end of the 3-aminopropyltrimethoxysilane molecule; in the second step, the glass surface reacts with the other end, or the silane end of the 3-aminopropyltrimethoxysilane-modified nucleic acid, thereby affixing the nucleic acid onto an underivatized glass surface.

As in example 1, the entire reaction is rapid, is characterized by a favorable equilibrium, and occurs under very mild conditions using a minimum of inexpensive reagents. Though there quite obviously are numerous ways to carry out either step of the reaction, the preferred method is shown in this and the following example.

Figure 2:
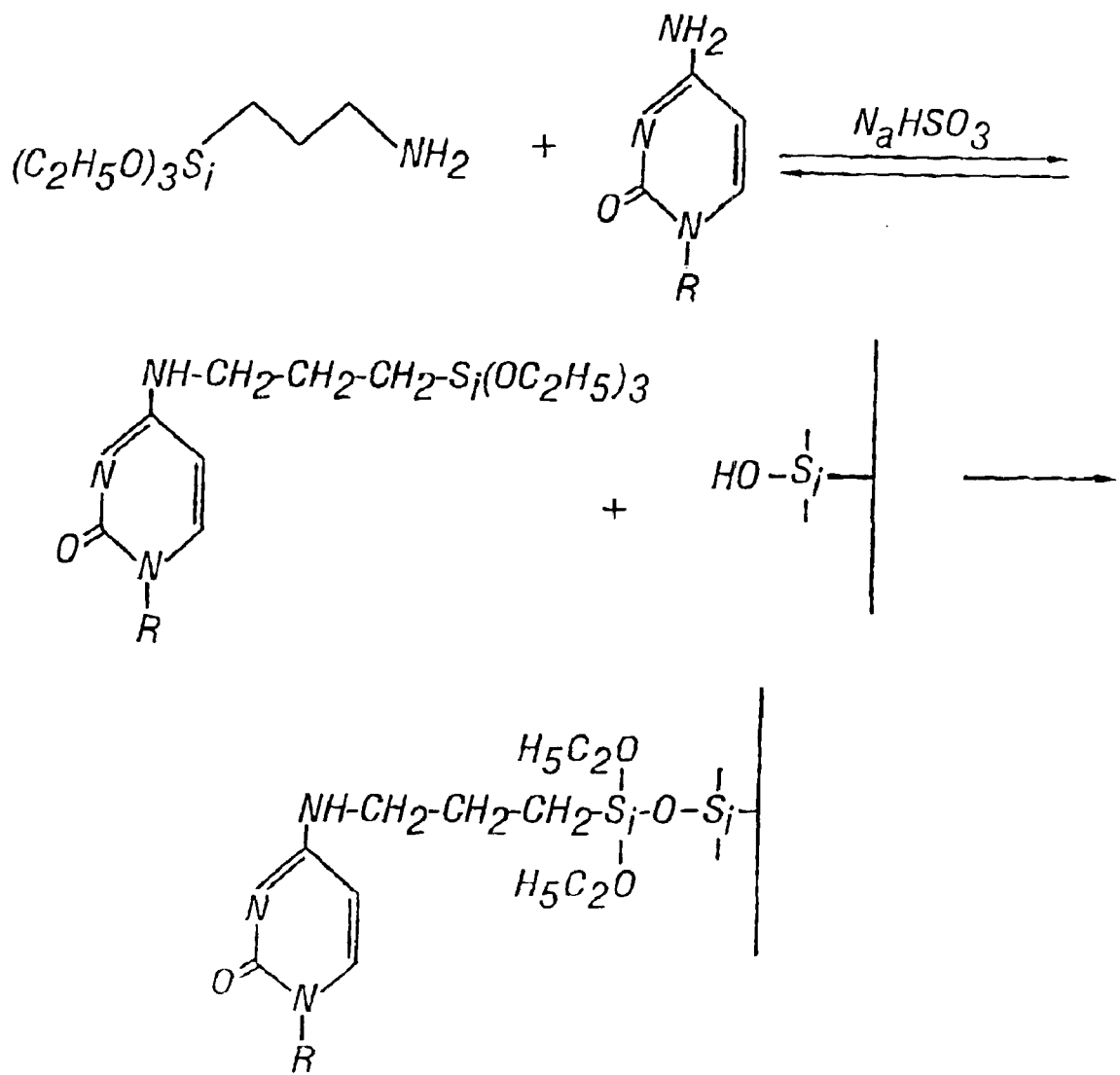
FIG. 2 depicts a coupling reaction of nucleic acid (in this instance DNA) with 3-aminoproplytriethoxysilane followed by the reaction of the newly modified DNA and the solid support (in this instance a glass surface). The final reaction product, the immobilized DNA, is shown at bottom.

As depicted in FIG. 2, a chemical compound having an amino group and an alkoxysilane—in this instance—NH$_2$ and triethyloxysilane, respectively-comprise the two ends of the compound; the two ends are connected by a propyl linkage. The compound shown is 3-aminopropyltriethoxysilane. In the first step, DNA is reacted with 3-aminopropyltriethoxysilane at neutral pH in the presence of sodium bisulfite, or equivalent.

The first reaction, leading to the derivatized DNA, is transamination reaction of the cytosine residues on nucleic acids. The second reaction, as in Example 1, involving immobilizing the derivatized DNA onto the glass surface, is a simple substitution reaction. It creates an Si—O—Si linkage in the glass surface and removes one of the alkoxy groups from the GPTS molecule.

Example 3

Preparation of a High Density Microarray using Modified Nucleic Acid

The following example describes making a high-density microarray of the invention.

Once the modified nucleic acids of the present invention, such as those described in Examples 1 and 2, are prepared, they can then be exploited in a variety of ways, including, e.g., to make a high density array. Again, these modified nucleic acids (particularly DNA) can be immobilized onto a glass surface simply by contacting the modified DNA onto the underivatized surface. The significance of this is, among other things, that spreading (migration of the DNA sought to be immobilized from the desired location) and non-specific probe sticking (caused by derivatization of the glass surface which creates a net positive electrostatic charge upon the surface which attracts the net negatively charged DNA) are essentially eliminated.

These advantages allow the creation of extraordinarily high-density microarrays, which is highly desirable. For instance, due to the elimination of spreading, and the effective elimination of probe sticking, a single small glass surface can contain virtually thousands of DNA samples to be tested, each of which is microscopic in size, all immobilized upon a single glass surface. Indeed, one can construct a microarray consisting of multiple single sample spots smaller than 50 microns placed upon a glass surface.

Figure 3A:
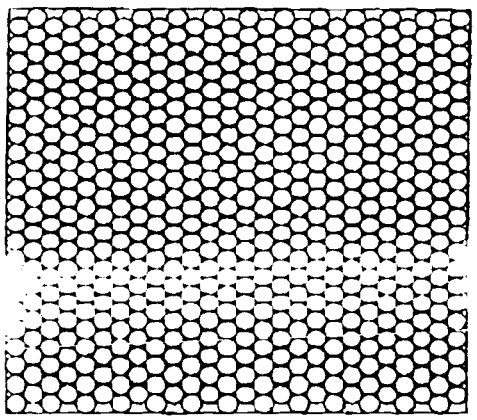
FIG. 3 depicts a device for making a high-density microarray; both a top (FIG. 3A) and a side view (FIG. 3B) are shown.
Figure 3B:
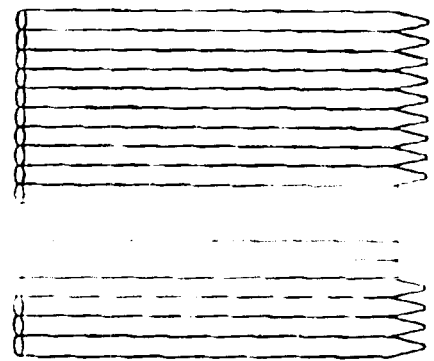

A high-density microarray consisting of multiple DNA samples of this type is also easily constructed in accordance with the present invention. The modified DNA can be prepared (for instance, in accordance with Examples 1 and 2) well in advance of actual use. These chemically modified DNA samples are analogous to "DNA chips" that can then be readily "imprinted" upon an unaltered glass sheet in, for instance, grid fashion. FIG. 3 illustrates one aspect of a device for preparing such a high-density microarray using the DNA chips of the present invention. In one preferred aspect, the device is made from a plurality of inexpensive commercially available capillary micropipets, preferably 10 cm micropipets, although other sizes will, of course, work. As depicted in FIG. 3 each 10 cm micropipet is pulled to make a taper at one end. They are arranged in a hexagonal close-packed array, bounded by a square frame. The micropipets can be glued to one another to form a stable unit within the frame. The tapered ends (FIG. 3B) are cut off and polished to optical flatness.

To prepare the microarray, the tips of the device are dipped into a multi-well container that contains the (chemically modified in accordance with the present invention) DNA samples to be tested, and whose wells are aligned with the micropipets of the device. Upon contact of the tips into the wells, a small portion of each DNA sample is deposited into the micropipet corresponding to the particular well by simple capillary action. The size of the spot can be carefully controlled by the size of the tapered end. Using this device and the DNA chips of the present invention, thousands of samples can be arrayed in a narrow area, simultaneously and without the need for expensive robotics. Indeed, the method (comprising the DNA chips and pipet device) of the present invention has been shown to be even more efficient than methods using high-speed spotting robots. Finally, the compounds, methods and devices of the present invention are readily incorporated into a prepackaged kit for commercial sale.

The high-density microarray of the present invention can also be readily incorporated into the microarray systems of the art, such as those disclosed in the art section above. For instance, fluorescent in situ hybridization (FISH) and the method described in Shalon (1996) 6 Genome Res. 639 (1996), describing a microarray system is presented for analyzing DNA samples that involves making microarrays of DNA samples on glass substrates, probing them by hybridization with complex fluorescent-labeled probes, and using a laser-scanning microscope to detect the fluorescent signals representing hybridization. Similarly, Sargent, et al. (U.S. Pat. No. 5,601,982) discloses a method and apparatus for determining the sequence of polynucleotides involving scanning the nucleic acids by scanning tunneling microscopy.

One skilled in the art recognizes that this invention is not limited to using only nucleic acids. Other biological molecules, such as biopolymers, e.g., DNA, RNA, proteins, peptides or polypeptides, and polysaccharides, can be directly activated using the methods of the invention, such as bifunctional silane compounds or other crosslinking reagents, resulting in an immobilized biologic molecule, e.g., a biopolymer, to a solid surface. This invention demonstrates that the target molecules to be arrayed (i.e., immobilized) are first modified so that they have gained a binding affinity for solid surfaces without losing their probing (e.g., hybridization) abilities. Because modification is a separate process, virtually any biological molecule can be modified and arrayed (immobilized). Thus, a skilled artisan realizes that this invention is not limited to nucleic acids, but can also be used for a spectrum of biological molecules.

Example 4

Preparation of Modified Nucleic Acids

The following example demonstrates methods for preparing modified biological molecules of the invention by describing the modification of nucleic acids.

Figure 4:
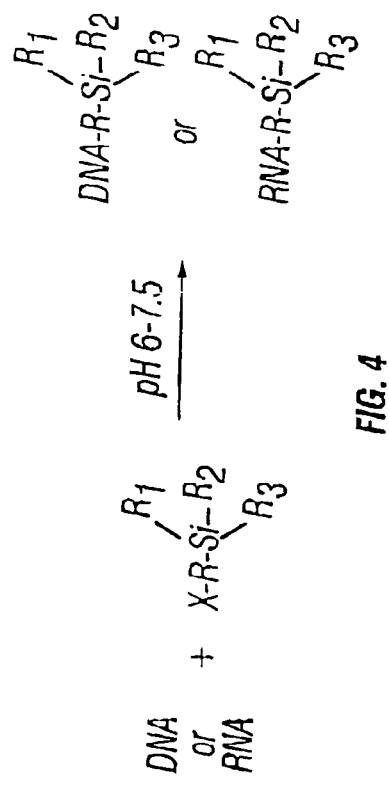
FIG. 4 depicts the silanization of nucleic acid through alkylation of halogen-containing silane compounds.

Using Halogenated Silanes: This example describes another form of modified nucleic acid of the present Invention. Again, the purpose of the chemical modification disclosed and claimed here is to enable to nucleic acid to be readily affixed to an underivatized solid surface, e.g., ordinary quartz glass. According to FIG. 4, a modified nucleic acid in accordance with the present invention is prepared by reacting unmodified nucleic acid under near neutral pH with suitable silane compounds. The "X" in FIG. 4 can refer to any halide, preferably Cl, Br, or I; $R_1$, $R_2$ and $R_3$, can be the same or different, including, —$OCH_3$, and —$OC_2H_5$. In particularly, preferred aspects, the halogenated silane depicted to the left of the arrow in FIG. 4 is 8-bromocytltrichlorosilane, 8-bromo-cytltrimethoxysilane, 4-chlorobutylmethyldichlorosilane, and 3-iodopropyltrimethoxysilane.

The conversion depicted in FIG. 4 was performed as follows. The halogenated silane was dissolved in dimethylformamide (DMF) at a concentration of about 30 mM. Next, 3 $\mu$g to 10 $\mu$g of nucleic acid was dissolved in 100 $\mu$l of 0.01 M phosphate buffer (pH 7.0). Then 1 to 3 $\mu$g of 30 mM halogenated silane was added, the solution is then mixed well, and allowed to react at about 37° C. for about 3 hours (alternatively, it can be reacted at ambient temperature overnight). After reaction, the desired product—the modified nucleic acid—is purified by ethanol precipitation; then the modified nucleic acid is dissolved in water.

Example 5

Preparation of Arrays and Controlling Spot (Cluster) Density and Size

The following example demonstrates an exemplary method for manufacturing the arrays, or "biochips" of the invention.

As discussed throughout the present application, one particular advantage of the present invention is that it allows the investigator to prepare unusually high-density microarrays to conduct nucleic acid studies. This example is best understood in relation to example 3, which disclosed the preparation of a high-density microarray in accordance with the present invention. This example discloses enhanced methods for controlling the size and density of the individual nucleic acid "spots" or "clusters" on the solid supports, in accordance with the present invention.

Small "spot" or "cluster" size, in relation to high-density microarrays, allows higher sample density (i.e., more samples per unit area) and superior detection sensitivity (because the signals are less diffuse). In the conventional solid support systems, the skilled artisan faces a crucial dilemma. An ordinary clean quartz glass surface—of the type used in the experiments described here—is very hydrophilic. Thus, nucleic acid samples will naturally tend to spread out when placed on the glass surface. Again, this is undesirable. To mitigate spreading, the skilled artisan can treat the surface to make it more hydrophobic—e.g., either pretreating the surface with a hydrophobic agent, or simply by dehydrating the surface. Naturally, either of these options makes the glass surface less reactive towards silane-modified nucleic acids.

Figure 6:
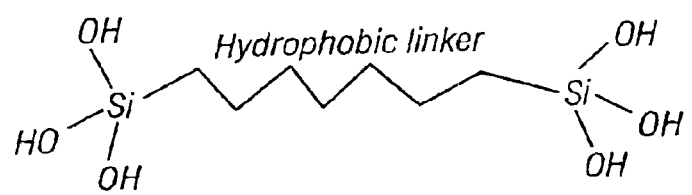
FIG. 6 is a schematic representation of one aspect of the present invention showing silane linkers by hydrophobic linkers.

In a family of aspects of the present invention discussed in this example, the skilled artisan is spared this dilemma. More specifically, spreading can be eliminated yet the reactivity of the surface towards the modified nucleic acids can be maintained through the use of another type of silanes of the present invention. For instance, one quite general aspect of these silanes after hydrolysis contains an $Si(OH)_3$ at each end, linked by a hydrophobic group. See FIG. 6. Any of a variety of hydrophobic linkers can be used. Particularly preferred aspects include: 1,6-Bis-trichlorosilyhexane, 1,8-Bis-trichlorosilyloctane, 1,6-Bis-trimethoxysilyhexane, and 1,4 Bis-trimethoxysilylethylbenzene. Thus, according to these aspects of the present invention, one end of the silane attaches to the surface, and the other end remains reactive to the modified biological molecule, e.g., nucleic acid. The hydrophobic linker confers hydrophobicity to the surface. Thus, the skilled artisan can readily see how the electrostatic properties of the surface (hydrophobic versus hydrophilic) can be readily modulated—e.g., the chain length of the linker can be adjusted to control hydrophobicity, and the surface reactivity can be controlled by adjusting the amount of silane contacted with the surface.

To prepare the solid supports in accordance with this aspect of the present invention, the glass surface was cleaned by slowly boiling in 3 M HCl for about 2 hrs in a fume hood. Next, the surfaces were rinsed with deionized water then kept in 0.1 M HCl until ready for use. When ready for use, the surfaces were rinsed with doubly distilled deionized water to remove any extant acid, then rinsed in absolute ethanol. Next, the surfaces were immediately transferred to an ethanol solution containing 0.0005% to 0.002% of the bi-functional silanes of this aspect of the invention. The surfaces were then treated at room temperature for about 48 hours. The surfaces were then rinsed with ethanol and air dried. Finally, the glass surfaces were stored in a dust-free environment until ready for use.

Example 6

Preparation of Modified Nucleic Acids Using Amine-Containing Silane Compounds

Figure 5A:
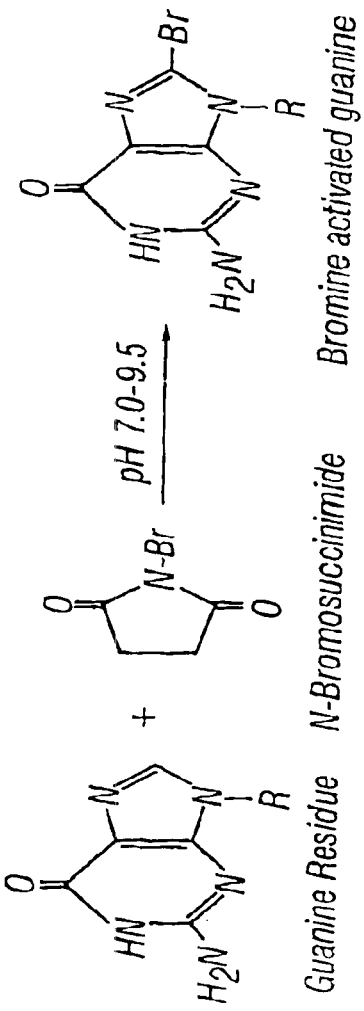
FIG. 5a depicts the first step in the silanization of nucleic acid using amine-containing silane compounds. In this case, the reaction occurs preferentially at the guanine base at neutral and slightly basic pH.
Figure 5B:
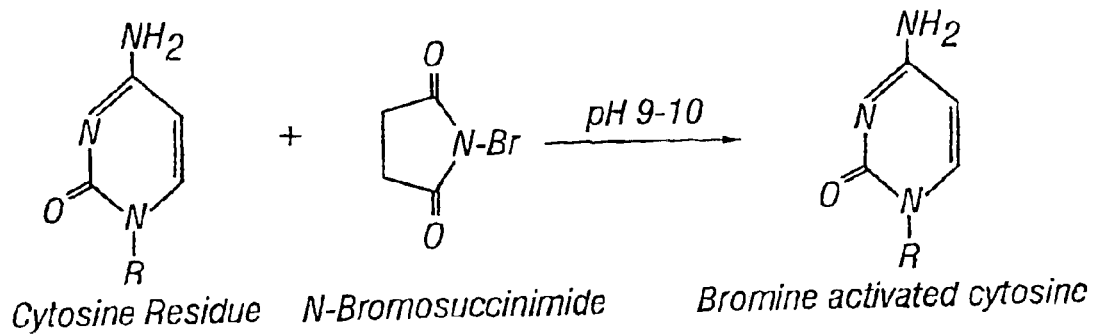
FIG. 5b depicts the first step in the silanization of nucleic acid using amine-containing silane compounds. In this case, the reaction occurs preferentially at the cytosine base at more basic pH.
Figure 5C:
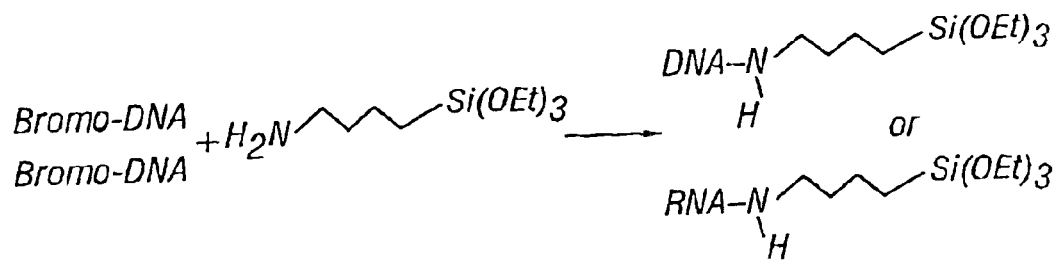
FIG. 5c depicts the second and final step in the silanization of nucleic acid using amine-containing silane compounds.

The following example describes another form of modified nucleic acid of the present invention. In this family of aspects, the modified nucleic acid is prepared by reacting pristine nucleic acids with an amine-containing silane. Heuristically, the derivatization of nucleic acid with amine-containing silanes is comprised of two steps: (1) the halogenation (or bromination, as shown) of the nucleic acid (FIG. 5a, 5b); and (2) the derivatization of the halogenated nucleic acid (FIG. 5c). As depicted in FIG. 5a, 5b, the reaction can occur in the presence of N-bromosuccinimide under mild pH conditions; varying either of these reaction variables allows the skilled biochemist to control the reaction rate. Also as evidenced by FIG. 5a, 5b, the reaction normally occurs at the guanine or cytosine base depending upon the pH—i.e., neutral to slightly basic pH favors reaction at the guanine residue, more basic pH favors reaction at the cytosine residue.

Slightly different reaction protocols are preferably used depending upon whether the nucleic acid is DNA or RNA. For DNA, 5 µg of DNA was dissolved in 100 µl of 0.1 M NaHCO$_3$, to reach a pH of about 9.5. This solution is kept on ice for about 5 minutes. Contemporaneously, a fresh N-bromosuccinimide solution at concentration of about 10 mM was prepared and also chilled on ice. Next, 1 µl of the N-bromosuccinimide solution is added to the DNA solution; the solution was then stirred vigorously (to vortex). The reaction was then allowed to proceed on ice for about 15 minutes. Next, 10 µl of 0.5 M aminosilane solution at pH about 9.5 to about 12, was added to the bromine-activated DNA solution; this new mixture was allowed to react at 65° C. for about 2 hours. Finally, the silane-modified DNA was purified by methods well known in the art; preferably, it is purified by ethanol precipitation, or equivalent procedures.

For RNA, a similar, though slightly different protocol was used: 5 µg of RNA was dissolved in 100 µl of 0.1 M phosphate buffer, to reach a pH of about 7.5. This solution is kept on ice for about 5 minutes. Contemporaneously, a fresh N-bromosuccinimide solution at concentration of about 10 mM was prepared and also chilled on ice. Next, 1 µl of the N-bromosuccinimide solution is added to the DNA solution; the solution was then stirred vigorously (to vortex). The reaction was then allowed to proceed on ice for about 15 minutes. Next, 10 µl of 1 M aminosilane solution at pH about 8.0, was added to the bromine-activated DNA solution; this new mixture was allowed to react at 45° C. for about 2 hours. Finally, the silane-modified DNA was purified by methods well known in the art; preferably, it is purified by ethanol precipitation, or equivalent procedures.

In these aspects the following silanes are available for these reasons:

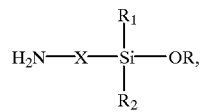

R can be —CH$_3$, or —C$_2$H$_5$;
R$_1$ can be H, —CH$_3$, —C$_2$H$_5$, —OCH$_3$, or —OC$_2$H$_5$;
R$_2$ can be H, —CH$_3$, —C$_2$H$_5$, —OCH$_3$, or —OC$_2$H$_5$;
Further any other amino silane compound after hydrolysis that takes the following form is useful:

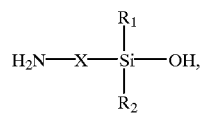

Example 7

Preparation of Modified Biological Molecules (Biopolymers) Using 3-glycidoxypropyltrimethoxysilane This example describes methods to modify biological molecules, e.g., nucleic acids, using bifunctional silane compounds.

The purpose of the chemical modification is to enable sample (the biological molecule) to be readily affixed to an underivatized solid surface. In this example, a biopolymer is modified by reaction with 3-glycidoxypropyltrimethoxysilane (GPTS).

Schematically, affixing the biopolymer to a solid surface consists essentially of two steps. In the first, the biopolymer reacts with the epoxide end of the GPTS molecule; in the second step, the glass surface reacts with the other end, or the silane end of the GPTS-modified biopolymer, thereby affixing the biopolymer onto an underivatized surface.

A skilled artisan recognizes that a variety of bifunctional crosslinking reagents could be used in the present invention (see above). Crosslinking reagents and the conditions required for their use are well known in the art, thus, one skilled in the art would be able to extrapolate the information provided by this application and utilize specific crosslinking reagents and conditions to obtain a specific modified biopolymer.

Example 8

Preparation of Modified Small Molecules

This example describes methods to modify biological molecules which may not be described as biopolymers. As described above, any biological molecule can be incorporated into the compositions and methods of the invention. These non-biopolymers are first crosslinked to epoxide silane-activated biopolymers, e.g., biopolymers activated according to Example 7. The crosslinking of these non-biopolymers, which are typically small molecules, increases the size and stability of the molecule. Once the non-biopolymer is crosslinked to an activated biopolymer, e.g., polyethylene glycol (PEG) or DNA, these crosslinked molecules can be immobilized on a solid surface by direct deposition and curing under proper conditions.

Example 9

Silanization of Amine-Containing Biopolymers such as Proteins and Polypeptides (e.g., Antibodies), Polysaccharides and Lipids This example describes methods to modify amine-containing biological molecules by silanization. Such biological molecules include peptides and polypeptides (e.g., antibodies), lipids and polysaccharides, in addition to nucleic acids comprising amine groups. Nucleic acids comprising amine groups include, e.g., nucleotide compositions containing aminooxy moieties, as described in U.S. Pat. No. 6,127,533.

Figure 7:
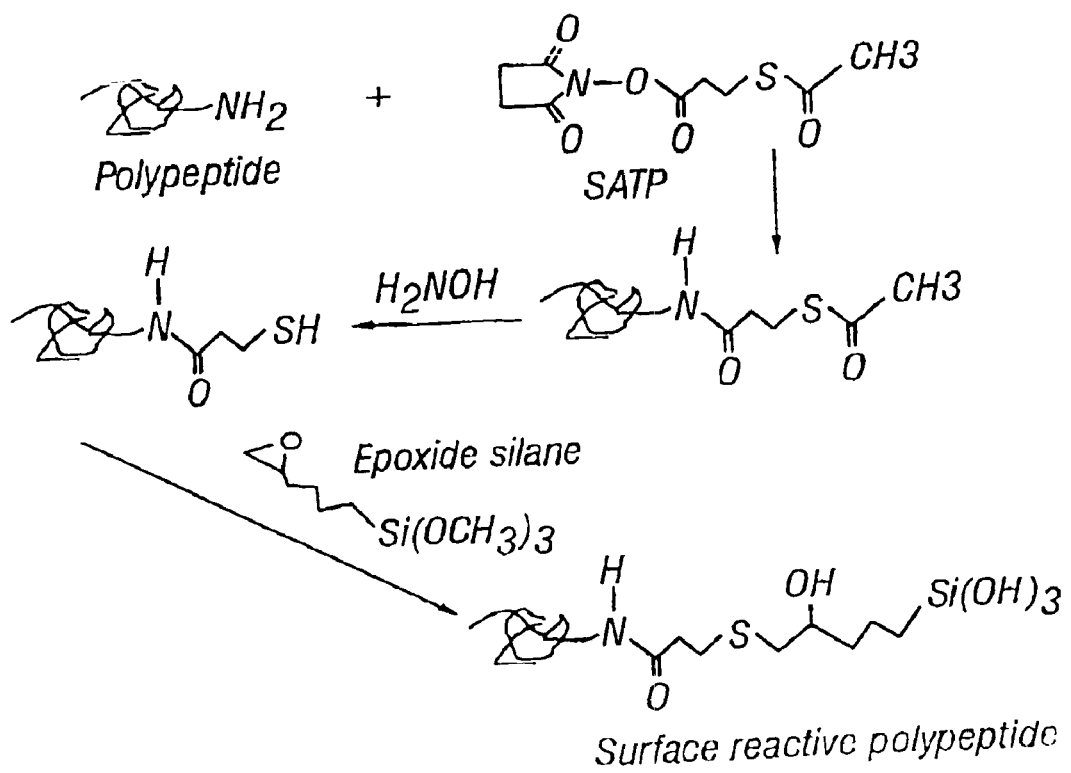
FIG. 7 is a schematic representation of an exemplary reaction wherein a biological molecule, a polypeptide, is modified, or "activated," by a method comprising use of succinimidyl acetylthiopropionate (SATP) to introduce an active sulfhydryl functional group, as described in detail in Example 9, below.

Biopolymers are effectively silanized and arrayed onto glass surfaces. Biopolymers are first treated with 2-iminothiolane (commonly known as "Traut's Reagent") or N-succinimidyl S-acetylthioacetate (SATA) or succinimidyl acetylthiopropionate (SATP) to introduce an active sulfhydryl functional group. The activated biopolymers are silanized by reacting with the epoxide silane compound as described previously under mild conditions. A typical reaction is depicted in FIG. 7; this example uses SATP and an epoxide silane comprising —Si(OCH$_3$)$_3$.

Antibodies are silanized by various methods. One such method is to first dissolve an antibody in 0.1 M sodium phosphate buffer (pH 7.3) with 50 mM NaCl and 10 mM EDTA at a concentration of about 1 to 3 mg/ml. Then, add 5 µl of 100 mM SATA or SATP in a DMSO solution to 1 ml antibody solution and react at room temperature (RT) overnight. Next, add 100 μM of 1 M hydroxylamine hydrochloride and react at RT for one hour. After the RT activation, add 10 μM of 0.2 M 3-glycidoxypropyltrimethoxysilane (epoxide silane) and react at RT for about 5 hours. Upon completion of all reactions, antibodies are purified by gel filtration on a Sephadex G25 column, or equivalent. The modified antibody is fixed on a glass surface by direct deposition.

All patents, publications mentioned in this specification are indicative of the level of those skilled in the art to which the invention pertains. All patents, publications herein are incorporated by reference to the same extent as if each individual publication was specifically and individually indicated to be incorporated by reference.

One skilled in the art will readily appreciate that the present invention is well adapted to carry out the objects and obtain the ends and advantages mentioned as well as those inherent therein. The chemically modified nucleic acids, their attachment to solid support, along with the sequences, methods, procedures, assays, molecules, devices and specific compounds described herein are presently representative of the preferred aspects are exemplary and are not intended as limitations on the scope of the invention. Changes therein and other uses will occur to those skilled in the art which are encompassed within the spirit of the invention and are defined by the scope of the claims.

What is claimed is:

1. A composition comprising a nucleic acid or an analog or mimetic thereof, a polysaccharide or an analog or mimetic thereof, a lipid or an analog or mimetic thereof, a peptidomimetic or a nonbiopolymeric small molecule modified by reaction with a compound having the formula: $R_1$—X—$R_2$, wherein $R_1$ comprises a cyclic ether group or an amino group, $R_2$ comprises an alkoxysilane group and X comprises a moiety for linking the cyclic ether group or the amino group to the alkoxysilane group, and wherein the modified composition is soluble in aqueous solution.

2. The composition of claim 1, wherein the cyclic ether comprises a compound comprising an epoxide group.

3. The composition of claim 2, wherein the epoxide comprises ethylene oxide.

4. The composition of claim 1, wherein the cyclic ether comprises an oxirane group.

5. The composition of claim 1, wherein the cyclic ether comprises a compound comprising an aromatic hydrocarbon epoxide group.

6. The composition claim 1, wherein the $R_1$ group reacts with the nucleic acid or an analog or mimetic thereof, the polysacchande or an analog or mimetic thereof, the lipid or an analog or mimetic thereof, or the peptidomimetic.

7. The composition of claim 6, wherein the $R_1$ group is covalently bound to the nucleic acid or an analog or mimetic thereof, the polysaccharide or an analog or mimetic thereof, the lipid or an analog or mimetic thereof, the peptidomimetic or the small molecule.

8. The composition of claim 1, wherein the composition comprises a modified peptidomimetic.

9. The composition of claim 1, wherein the composition comprises a modified polysaccharide or an analog or a mimetic thereof.

10. The composition of claim 1, wherein the composition comprises a modified lipid or an analog or a mimetic thereof.

11. The composition claim 1, wherein the composition comprises a modified small molecule.

12. The composition of claim 1, wherein the composition comprises a modified nucleic acid or an analog or mimetic thereof.

13. The composition of claim 12, wherein the nucleic acid comprises a DNA or an RNA.

14. The composition of claim 12, wherein the nucleic acid reacts with the $R_1$ group at its 5' end.

15. The composition of claim 12, wherein the nucleic acid is an oligonucleotide.

16. The composition claim 12, wherein the nucleic acid comprises a telomeric structure.

17. The composition of claim 12, wherein the nucleic acid comprises a chromatin structure.

18. The composition of claim 1, wherein cyclic ether comprises an epoxide group and the alkoxysilane is —Si(OCH$_3$)$_3$, —Si(OC$_2$H$_5$)$_3$, —Si(OCH$_3$)H$_2$, —Si(OCH$_3$)(CH$_3$)$_2$, or —Si(OCH)$_3$)$_2$ CH$_3$.

19. The composition of claim 1, wherein cyclic ether comprises an epoxide group and the compound is 3-glycidoxypropyltrimethoxysilane (GPTS).

20. The composition of claim 1, wherein the $R_1$ amino group comprises a primary amino group.

21. The composition of claim 1, wherein $R_1$ comprises an amino group and the alkoxysilane is selected from the group consisting of —Si(OCH$_3$)$_3$, —Si(OC$_2$H$_5$)$_3$ and

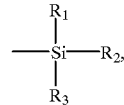

wherein $R_1$, $R_2$ and $R_3$ are selected from the group consisting of —H, —CH$_3$, —OCH$_3$, and —OC$_2$H$_5$, and provided that at least one of $R_1$, $R_2$ or $R_3$ is either —OCH$_3$ or —OC$_2$H$_5$.

22. The composition of claim 1, wherein $R_1$ comprises an amino group and the compound comprises 3-aminopropyltriethoxysilane.

23. An article of manufacture comprising an arrayed plurality of biological molecules covalently bound to a surface,
wherein before attachment to the surface, the biological molecules are modified by reaction with a compound having the formula: $R_1$—X—$R_2$, wherein $R_1$ is a cyclic ether group or an amino group, $R_2$ is an alkoxysilane group and X is a moiety chemically suitable for linking the cyclic ether group or the amino group to the alkoxysilane group, and upon attachment to the surface the modified biological molecules are covalently bound to the surface;
wherein each biological molecule is attached to the surface on at least one discrete and known location to form a cluster of substantially identical biological molecules.

24. The article of manufacture of claim 23, wherein the surface is glass.

25. The article of manufacture of claim 23, wherein the surface is mica or quartz.

26. The article of manufacture of claim 23, wherein the surface is a metal oxide surface.

27. The article of manufacture of claim 23, wherein the metal oxide surface is selected from the group consisting of an alumina (Al$_2$O$_3$), a titania (TiO$_2$), a SnO$_2$, a RuO$_2$, or a PtO$_2$.

28. The article of manufacture of claim 23, wherein the surface is selected from the group consisting of a polystyrene, a polyester, a polycarbonate, a polyethylene, a polypropylene, and a nylon.

29. The article of manufacture of claim 23, wherein the modified biological molecules are covalently bound to the surface via the $R_2$ group.

30. The article of manufacture of claim 23, wherein the biological molecules are derived from a human.

31. The article of manufacture of claim 23, wherein the biological molecules are derived from a mouse.

32. The article of manufacture of claim 23, wherein the biological molecules comprise a nucleic acid, or an analog or a mimetic thereof.

33. The article of manufacture of claim 23, wherein the nucleic acid comprises a DNA or an RNA.

34. The article of manufacture of claim 32, wherein the nucleic acid is an oligonucleotide.

35. The article of manufacture of claim 23, wherein the biological molecule comprises a polypeptide, a peptide, or a peptidomimetic.

36. The article of manufacture of claim 23, wherein the biological molecule comprises a polysaccharide, or an analog or a mimetic thereof.

37. The article of manufacture of claim 23, wherein the biological molecule comprises a lipid, or an analog or a mimetic thereof.

38. The article of manufacture of claim 23, wherein the biological molecule comprises a small molecule.

39. The article of manufacture of claim 32, wherein the nucleic acid reacts with the $R_1$ group at the 5' end.

40. The article of manufacture of claim 32, wherein the nucleic acid comprises a plurality of fragments of a genomic nucleic acid.

41. The article of manufacture of claim 40, wherein the genomic nucleic acid is derived from a normal cell.

42. The article of manufacture of claim 40, wherein the genomic nucleic acid is derived from a cell suspected of having a chromosomal defect or abnormality.

43. The article of manufacture of claim 42, wherein the cell suspected of having a chromosomal defect or abnormality is a tumor cell.

44. The article of manufacture of claim 40, wherein the fragments of genomic nucleic acid further comprise a cloning vehicle.

45. The article of manufacture of claim 44, wherein the cloning vehicle comprises a bacterial artificial chromosome (BAC).

46. The article of manufacture of claim 44, wherein the cloning vehicle comprises a plasmid, a cosmid, a bacteriophage P1-derived vector (PAC), a yeast artificial chromosome (YAC) or a mammalian artificial chromosome (MAC).

47. The article of manufacture of claim 32, wherein the nucleic acid comprises a plurality of CpG island tags.

48. The article of manufacture of claim 40, wherein the fragments of genomic nucleic acid comprise sequences representing at least one substantially complete chromosome or at least one defined section of a chromosome.

49. The article of manufacture of claim 40, and each genomic nucleic acid fragment have been mapped to a known location on a chromosome.

50. The article of manufacture of claim 40, wherein genomic nucleic acid fragments have a size no more than about 1.2 megabase.

51. The article of manufacture of claim 50, wherein genomic nucleic acid fragments are no more than about 1.0 megabase in size.

52. The article of manufacture of claim 23, wherein each cluster consists of between about 10 and 200 substantially identical copies of a biological molecule.

53. The article of manufacture of claim 23, wherein the surface consists of less than about 400 clusters per square centimeter.

54. The article of manufacture of claim 23, wherein each cluster is about 50 microns in diameter or smaller.

55. The article of manufacture of claim 54, wherein each cluster is about 25 microns in diameter or smaller.

56. An article of manufacture comprising an array of cloned genomic nucleic acid fragments representing a defined subsection of or a substantially complete chromosome, wherein before attachment to the surface, the cloned fragments are modified by reaction with a compound having the formula: $R_1$—X—$R_2$, wherein $R_1$ is an epoxide group, $R_2$ is an alkoxysilane group and X is a moiety chemically suitable for linking the epoxide group and the alkoxysilane group, and the modified cloned fragments are covalently bound to the surface;

wherein each array-bound cloned fragment has been mapped to a known location on the chromosome.

57. A kit comprising an article of manufacture as set forth in claim 23 and printed matter, wherein the printed matter comprises instructions on hybridizing a sample of nucleic acid to an array-bound nucleic acid.

58. A method for making a modified biological molecule comprising (a) providing a biological molecule;

(b) providing a compound having the formula: $R_1$—X—$R_2$, wherein $R_1$ comprises an amino group, $R_2$ comprises an alkoxysilane group and X comprises a moiety chemically suitable for linking the cyclic ether group or the amino group to the alkoxysilane group; and (c) reacting the biological molecule with the compound, thereby modifying the biological molecule with the compound, wherein the modified biological molecule is soluble in aqueous solution.

59. A method for making an article of manufacture comprising an arrayed plurality of biological molecules covalently bound to a surface comprising (a) providing a biological molecule;

(b) providing a compound having the formula: $R_1$—X—$R_2$, wherein $R_1$ comprises a cyclic ether group or an amino group, $R_2$ comprises an alkoxysilane group and X comprises a moiety chemically suitable for linking the cyclic ether group or the amino group to the alkoxysilane group;

(c) providing a surface comprising hydroxyl groups;

(d) reacting the biological molecule with the compound, thereby modifying the biological molecule with the compound to obtain a resulting modified molecule that is soluble in aqueous solution; and (e) depositing a plurality of modified biological molecules on the surface as discrete clusters, wherein the modified biological molecule is attached to the surface on at least one discrete and known location to form a cluster of substantially identical biological molecules and the array comprises a plurality of clusters.

60. A modified biological molecule comprising a biological molecule modified by reaction with a compound having the formula: $R_1$—X—$R_2$, wherein $R_1$ comprises a cyclic ether group, $R_2$ comprises an alkoxysilane group and X comprises a moiety chemically suitable for linking the cyclic ether group to the alkoxysilane group and the cyclic ether comprises an oxirane group, wherein the biological molecule is selected from the group of a nucleic acid or an analog or mimetic thereof, a polysaccharide or an analog or mimetic thereof, a lipid or an analog or mimetic thereof, a peptidomimetic and a nonbiopolyrneric small molecule.

61. A modified biological molecule comprising a biological molecule modified by reaction with a compound having the formula: R₁—X—R₂, wherein R₁ comprises a cyclic ether group, R₂ comprises an alkoxysilane group and X comprises a moiety chemically suitable for linking the cyclic ether group to the alkoxysilane group and the cyclic ether comprises a compound comprising an aromatic hydrocarbon epoxide group, wherein the biological molecule is selected from the group of a nucleic acid or an analog or mimetic thereof, a polysaccharide or an analog or mimetic thereof, a lipid or an analog or mimetic thereof, a peptidomimetic and a nonbiopolymeric small molecule.

62. A modified biological molecule comprising a biological molecule modified by reaction with a compound having the formula: R₁—X—R₂, wherein R₁ comprises a cyclic ether group or an amino group, R₂ comprises an alkoxysilane group and X comprises a moiety chemically suitable for linking the cyclic ether group or the amino group to the alkoxysilane group and the R₁ group reacts with the biological molecule, wherein the biological molecule is selected from the group of a nucleic acid or an analog or mimetic thereof; a polysaccharide or an analog or mimetic thereof, a lipid or an analog or mimetic thereof, a peptidomimetic and a nonbiopolymeric small molecule, wherein the modified molecule is soluble in aqueous solution.

63. A modified biological molecule comprising a biological molecule modified by reaction with a compound having the formula: R₁—X—R₂, wherein R₁ comprises a cyclic ether group or an amino group, R₂ comprises an alkoxysilane group and X comprises a moiety chemically suitable for linking the cyclic ether group or the amino group to the alkoxysilane group and the R₁ group is covalently bound to the biological molecule, wherein the biological molecule is selected from the group of a nucleic acid or an analog or mimetic thereof; a polysaccharide or an analog or mimetic thereof, a lipid or an analog or mimetic thereof; a peptidomimetic and a nonbiopolymeric small molecule, wherein the modified biological molecule is soluble in aqueous solution.

64. A modified biological molecule comprising a biological molecule modified by reaction with a compound having the formula: R₁—X—R₂, wherein R₁ comprises a cyclic ether group or an amino group, R₂ comprises an alkoxysilane group and X comprises a moiety chemically suitable for linking the cyclic ether group or the amino group to the alkoxysilane group and the biological molecule comprises a nucleic acid or an analog or mimetic thereof, wherein the modified biological molecule is soluble in aqueous solution.

65. The modified biological molecule of claim 64, wherein the nucleic acid comprises a DNA or an RNA.

66. The modified biological molecule of claim 64, wherein the nucleic acid reacts with the R₁ group at its 5' end.

67. The modified biological molecule of claim 64, wherein the nucleic acid is an oligonucleotide.

68. The modified biological molecule of claim 64, wherein the nucleic acid comprises a telomeric structure.

69. The modified biological molecule of claim 64, wherein the nucleic acid comprises a chromatin structure.

70. A modified biological molecule comprising a biological molecule modified by reaction with a compound having the formula: R₁—X—R₂, wherein R₁ comprises an amino group, R₂ comprises an alkoxysilane group and X comprises a moiety chemically suitable for linking the amino group to the alkoxysilane group and the alkoxysilane is selected from the group consisting of —Si(OCH₃)₃, —Si(OC₂H₅)₃ and

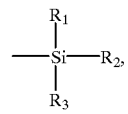

wherein R₁, R₂ and R₃ are selected from the group consisting of —H, —CH₃, —OCH₃, and —OC₂H₅, and provided that at least one of R₁, R₂ or R₃ is either —OCH₃ or —OC₂H₅.

71. A composition comprising a biological molecule modified by reaction with a compound having the formula: R₁—X—R₂, wherein R₁ comprises an amino group, R₂ comprises an alkoxysilane group and X comprises a moiety chemically suitable for linking the amino group to the alkoxysilane group, wherein the modified biological molecule is soluble in aqueous solution.

72. The composition of claim 71, wherein the biological molecule comprises a polypeptide, a peptide or a peptidomimetic.

73. The composition of claim 71, wherein the biological molecule comprises a polysaccharide, or an analog or a mimetic thereof.

74. The composition of claim 71, wherein the biological molecule comprises a lipid, or an analog or a mimetic thereof.

75. The composition of claim 71, wherein the biological molecule comprises a small molecule.

76. The composition of claim 71, wherein the biological molecule comprises a nucleic acid or an analog or mimetic thereof.

77. The composition of claim 76, wherein the nucleic acid comprises a DNA or an RNA.

78. An article of manufacture comprising a plurality of biological molecules covalently bound to a surface, wherein, before attachment to the surface, the biological molecules are modified by reaction with a compound having the formula:

R₁—X—R₂, wherein R₁ comprises an amino group, R₂ comprises an alkoxysilane group and X comprises a moiety chemically suitable for linking the amino group to the alkoxysilane group, and upon attachment to the surface the modified biological molecules are covalently bound to a surface.

79. A method for making an article of manufacture having biological molecules covalently bound to a surface, the method comprising (a) providing each of a biological molecule; a compound having the formula: R₁—X—R₂, wherein R₁ comprises an amino group, R₂ comprises an alkoxysilane group and X comprises a moiety chemically suitable for linking the amino group to the alkoxysilane group; and a surface comprising hydroxyl groups;

(b) reacting the biological molecule with the compound, thereby modifying the biological molecule with the compound; and (c) depositing a plurality of modified biological molecules on a surface of the article of manufacture.

* * * * *

UNITED STATES PATENT AND TRADEMARK OFFICE
CERTIFICATE OF CORRECTION

PATENT NO. : 6,979,728 B2  Page 1 of 1
DATED : December 27, 2005
INVENTOR(S) : Allan Bradley, Wei-Wen Cai and Upendra Marathi It is certified that error appears in the above-identified patent and that said Letters Patent is hereby corrected as shown below:

Column 27,
Line 49, "polysacchande" should read -- polysaccharide --.
Line 63, "The composition claim 1" should read -- The composition of claim 1 --.

Column 28,
Line 7, "The composition claim 12" should read -- The composition of claim 12 --.

Column 30,
Line 65, "nonbiopolyrneric" should read -- nonbiopolymeric --.

Column 31,
Lines 33 and 34, "mimetic thereof;" should read -- mimetic thereof, --.

Signed and Sealed this

Fourteenth Day of March, 2006

JON W. DUDAS
*Director of the United States Patent and Trademark Office*

UNITED STATES PATENT AND TRADEMARK OFFICE
CERTIFICATE OF CORRECTION

PATENT NO.         : 6,979,728 B2
APPLICATION NO.    : 09/853343
DATED              : December 27, 2005
INVENTOR(S)        : Allan Bradley, Wei-Wen Cai and Upendra Marathi It is certified that error appears in the above-identified patent and that said Letters Patent is hereby corrected as shown below:

At Column 1, after the title and before the section entitled "CROSS-REFERENCES TO RELATED "APPLICATIONS," please insert the following sentences:

Certain embodiments disclosed herein were made with Government support under a grant from the National Institutes of Health, No. R21 CA83211. The Government may have certain rights.

Signed and Sealed this

Twenty-third Day of January, 2007

JON W. DUDAS
*Director of the United States Patent and Trademark Office*